United States Patent
Mandalam et al.

(10) Patent No.: US 8,097,458 B2
(45) Date of Patent: Jan. 17, 2012

(54) MICRO-CARRIER CULTURE SYSTEM FOR RAPID EXPANSION OF HUMAN EMBRYONIC STEM CELLS

(75) Inventors: Ramkumar Mandalam, Union City, CA (US); Chunhui Xu, Cupertino, CA (US); Joseph D. Gold, San Francisco, CA (US); Melissa K. Carpenter, Castro Valley, CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 12/763,884

(22) Filed: Apr. 20, 2010

(65) Prior Publication Data

US 2010/0203633 A1    Aug. 12, 2010

Related U.S. Application Data

(63) Continuation of application No. 12/710,078, filed on Feb. 22, 2010, which is a continuation of application No. 12/170,219, filed on Jul. 9, 2008, application No. 12/763,884, which is a continuation of application No. 10/235,094, filed on Sep. 4, 2002, now Pat. No. 7,410,798.

(60) Provisional application No. 60/317,478, filed on Sep. 5, 2001.

(51) Int. Cl.
*C12N 15/02* (2006.01)

(52) U.S. Cl. .................. 435/402; 435/403; 435/387

(58) Field of Classification Search .................. None
See application file for complete search history.

(56) References Cited

U.S. PATENT DOCUMENTS

| | | |
|---|---|---|
| 4,423,145 A | 12/1983 | Stampfer et al. |
| 4,829,000 A | 5/1989 | Kleinman et al. |
| 5,104,795 A | 4/1992 | Lee et al. |
| 5,166,065 A | 11/1992 | Williams et al. |
| 5,234,809 A | 8/1993 | Boom et al. |
| 5,332,672 A | 7/1994 | Conover et al. |
| 5,405,772 A | 4/1995 | Ponting |
| 5,411,883 A | 5/1995 | Boss et al. |
| 5,453,357 A | 9/1995 | Hogan |
| 5,464,764 A | 11/1995 | Capecchi et al. |
| 5,523,226 A | 6/1996 | Wheeler |
| 5,583,016 A | 12/1996 | Villeponteau et al. |
| 5,591,625 A | 1/1997 | Gerson et al. |
| 5,614,396 A | 3/1997 | Bradley et al. |
| 5,635,387 A | 6/1997 | Fei et al. |
| 5,639,618 A | 6/1997 | Gay |
| 5,643,761 A | 7/1997 | Fisher et al. |
| 5,672,499 A | 9/1997 | Anderson et al. |
| 5,789,158 A | 8/1998 | Knowles et al. |
| 5,840,484 A | 11/1998 | Seilhamer et al. |
| 5,843,780 A | 12/1998 | Thomson |
| 5,856,136 A | 1/1999 | Au-Young |
| 5,906,940 A | 5/1999 | Wandrey et al. |
| 5,914,268 A | 6/1999 | Keller et al. |
| 5,922,597 A | 7/1999 | Verfaillie et al. |
| 5,942,435 A | 8/1999 | Wheeler |
| 5,968,829 A | 10/1999 | Carpenter |
| 5,981,165 A | 11/1999 | Weiss et al. |
| 5,994,129 A | 11/1999 | Armstrong et al. |
| 6,022,742 A | 2/2000 | Kopf |
| 6,040,180 A | 3/2000 | Johe |
| 6,090,622 A | 7/2000 | Gearhart et al. |
| 6,200,806 B1 | 3/2001 | Thomson |
| 6,245,566 B1 | 6/2001 | Gearhart et al. |
| 6,261,556 B1 | 7/2001 | Weinrich et al. |
| 6,280,718 B1 | 8/2001 | Kaufman et al. |
| 6,458,589 B1 | 10/2002 | Rambhatla et al. |
| 6,642,048 B2 | 11/2003 | Xu et al. |
| 6,800,480 B1 | 10/2004 | Bodnar et al. |
| 6,833,269 B2 | 12/2004 | Carpenter |
| 6,875,607 B1 | 4/2005 | Reubinoff et al. |
| 7,005,252 B1 | 2/2006 | Thomson |
| 7,041,438 B2 | 5/2006 | Carpenter et al. |
| 7,413,904 B2 | 8/2008 | Gold et al. |
| 7,455,983 B2 | 11/2008 | Xu et al. |
| 2002/0081724 A1 | 6/2002 | Carpenter et al. |
| 2003/0017589 A1 | 1/2003 | Mandalam et al. |
| 2003/0113910 A1 | 6/2003 | Levanduski |
| 2003/0153082 A1 | 8/2003 | Bhatia |
| 2005/0037492 A1 | 2/2005 | Xu et al. |
| 2005/0037493 A1 | 2/2005 | Mandalam et al. |
| 2005/0148070 A1 | 7/2005 | Thomson et al. |
| 2005/0233446 A1 | 10/2005 | Parsons et al. |

FOREIGN PATENT DOCUMENTS

AU    729377 B2    2/2001

(Continued)

OTHER PUBLICATIONS

Shimazu et al. Morphogenesis of MDCK cell in a collagen gel matrix culture under stromal adipocyte-epithelial cell interaction. Kidney International, 2001, vol. 60, pp. 568-578.*

(Continued)

*Primary Examiner* — Deborah Crouch
(74) *Attorney, Agent, or Firm* — E. Stewart Mittler

(57) ABSTRACT

This disclosure provides an improved system for culturing human pluripotent stem cells. Traditionally, pluripotent stem cells are cultured on a layer of feeder cells (such as mouse embryonic fibroblasts) to prevent them from differentiating. In the system described here, the role of feeder cells is replaced by components added to the culture environment that support rapid proliferation without differentiation. Effective features are a suitable support structure for the cells, and an effective medium that can be added fresh to the culture without being preconditioned by another cell type. Culturing human embryonic stem cells in fresh medium according to this invention causes the cells to expand surprisingly rapidly, while retaining the ability to differentiate into cells representing all three embryonic germ layers. This new culture system allows for bulk proliferation of pPS cells for commercial production of important products for use in drug screening and human therapy.

24 Claims, 10 Drawing Sheets

FOREIGN PATENT DOCUMENTS

Figure 1:
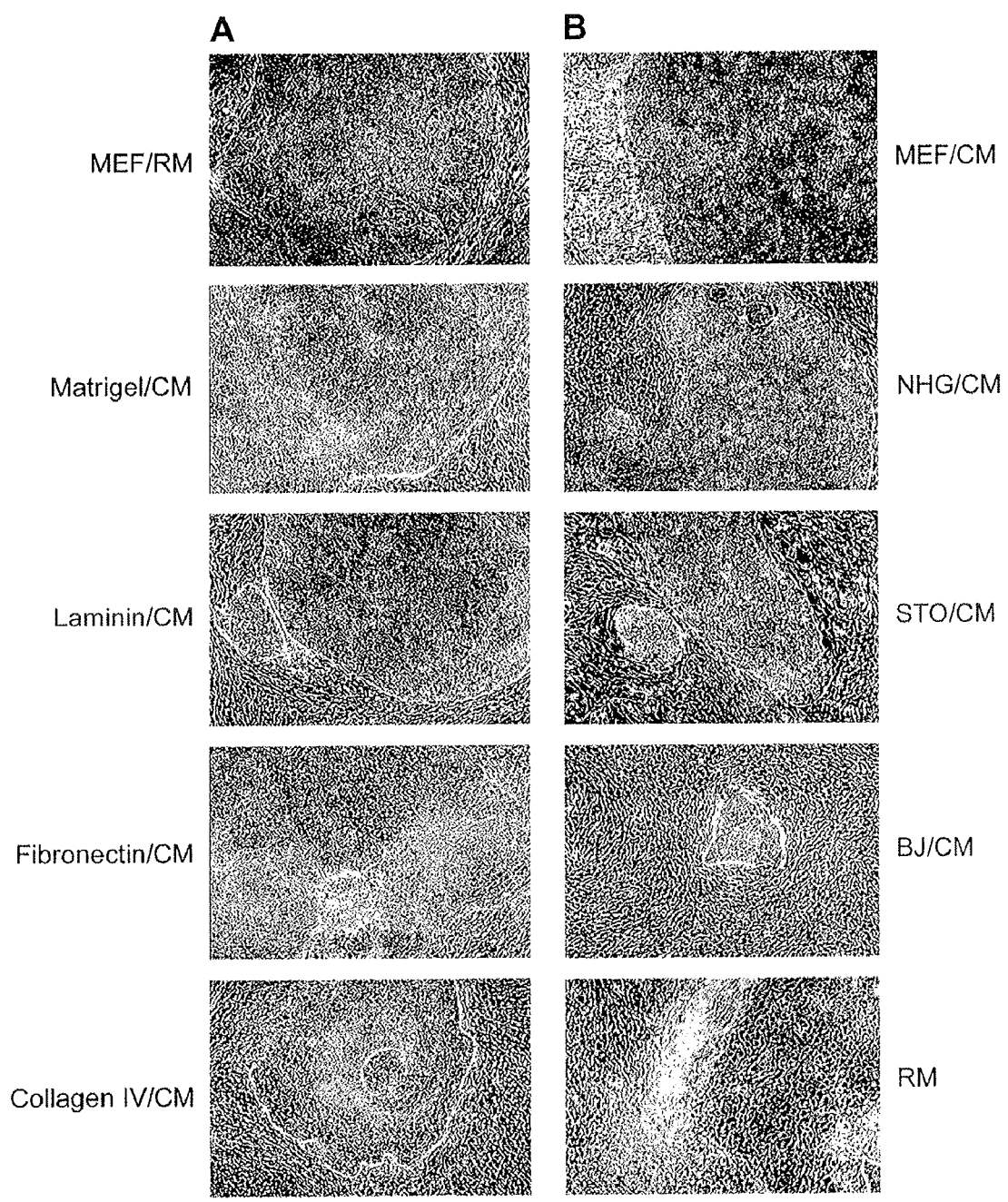

| | | |
|---|---|---|
| EP | 0 695 351 B1 | 12/1999 |
| FR | 2744133 A1 | 8/1997 |
| JP | 2001-17163 A | 1/2001 |
| WO | WO 94/07997 A1 | 4/1994 |
| WO | WO-95/00632 | 1/1995 |
| WO | WO 96/17627 A2 | 6/1996 |
| WO | WO 97/21802 A1 | 6/1997 |
| WO | WO 97/28253 A1 | 8/1997 |
| WO | WO 97/30151 A1 | 8/1997 |
| WO | WO 97/47734 A1 | 12/1997 |
| WO | WO 98/00540 A1 | 1/1998 |
| WO | WO 98/30678 A1 | 7/1998 |
| WO | WO 98/30679 A1 | 7/1998 |
| WO | WO 98/43679 A1 | 10/1998 |
| WO | WO 99/01552 A1 | 1/1999 |
| WO | WO 99/10535 A1 | 3/1999 |
| WO | WO 99/20741 A1 | 4/1999 |
| WO | WO 99/42122 A1 | 8/1999 |
| WO | WO 99/43785 A1 | 9/1999 |
| WO | WO-00/17323 | 3/2000 |
| WO | WO 01/51610 A1 | 7/2001 |
| WO | WO 01/51616 A2 | 7/2001 |
| WO | WO 01/66697 A2 | 9/2001 |
| WO | WO 01/81549 A2 | 11/2001 |
| WO | WO 03/000868 A1 | 1/2003 |
| WO | WO 03/004605 A2 | 1/2003 |
| WO | WO 03/006950 A2 | 1/2003 |
| WO | WO 03/020920 A1 | 3/2003 |
| WO | WO 03/050249 A2 | 6/2003 |
| WO | WO 03/050250 A2 | 6/2003 |
| WO | WO 03/050251 A2 | 6/2003 |
| WO | WO 2004/007696 A2 | 1/2004 |
| WO | WO 2004/055155 | 7/2004 |
| WO | WO 2005/090558 A1 | 9/2005 |
| WO | WO-2006/070370 | 7/2006 |
| WO | WO 2008/004990 A2 | 1/2008 |
| WO | WO 2008/015682 A2 | 2/2008 |

OTHER PUBLICATIONS

Mered et al. Cell Growth Optimization in Microcarrier Culture. In Vitro, 1980, pp. 859-865.*

Akiyama, H. et al., "Molecular Cloning and Biological Activity of a Novel Ha-Ras Suppressor Gene Predominantly Expressed in Skeletal Muscle, Heart, Brain, and Bone Marrow by Differential Display Using Clonal Mouse EC Cells, ATDC5," *J. Biol. Chem.* 274(45):32192 (1999).

Amit, M. et al., "Clonally derived human embryonic stem cell lines maintain pluripotency and proliferative potential for prolonged periods of culture," *Dev. Biol.* 227:271-8 (2000).

Amit, M. et al., "Feeder layer- and serum-free culture of human embryonic stem cells," *Biol. Reprod.* 70:837-45 (2004).

Amit, M. et al., "Human feeder layers for human embryonic stem cells," *Biol. Reprod.* 68:2150-6 (2003).

Amsterdam, A. et al., "Requirements for green fluorescent protein detection in transgenic zebrafish embryos," *Gene* 173:99-103 (1996).

Andrews, P., "Retinoic acid induces neuronal differentiation of a cloned human embryonal carcinoma cell line in vitro," *Dev. Biol.* 103:285-93 (1984).

Anzai, H. et al., "Self-renewal and differentiation of a basic fibroblast growth factor-dependent multipotent hematopoietic cell line derived from embryonic stem cells," *Dev. Growth Differ.* 41:51-8 (1999).

Aouadi, M. et al., "p38 mitogen-activated protein kinase activity commits embryonic stem cells to either neurogenesis or cardiomyogenesis," *Stem Cells* 24(5):1399-406 (2006).

Baribault, H. & Kemler, R., "Embryonic stem cell culture and gene targeting in transgenic mice," *Mol. Biol. Med.* 6:481-92 (1989).

Beattie, G. et al., "Activin A maintains pluripotency of human embryonic stem cells in the absence of feeder layers," *Stem Cells* 23:489-95 (2005).

Berger, C. & Sturm, K., "Self renewal of embryonic stem cells in the absence of feeder cells and exogenous leukaemia inhibitory factor," *Growth Factors* 14:145-59 (1997).

Bodnar, A. et al., "Extension of life-span by introduction of telomerase into normal human cells," *Science* 279:349-52 (1998).

Bongso, A. et al., "Improved quality of human embryos when co-cultured with human ampullary cells," *Hum. Reprod.* 4:706-13 (1989).

Bradley, A. et al., "Modifying the mouse: design and desire," *Biotechnol.* 10:534-9 (1992).

Brook, F. & Gardner, R., "The origin and efficient derivation of embryonic stem cells in the mouse," *Proc. Natl. Acad. Sci. USA* 97:5709-12 (1997).

Carnegie, J., "Immunolocalization of fibronectin and laminin within rat blastocysts cultured under serum-free conditions," *J. Reprod. Fertil.* 91:423-34 (1991).

Carninci, P. & Hayashizaki, Y., "High-efficiency full-length cDNA cloning," *Meth. Enzymol.* 303:19-44 (1999).

Carpenter, M. et al., "Enrichment of neurons and neural precursors from human embryonic stem cells," *Exp. Neurol.* 172(2):383-97 (2001).

Carpenter, M. et al., "Properties of four human embryonic stem cell lines maintained in a feeder-free culture system," *Dev. Dyn.* 229:243-58 (2004).

Chambers, I. et al., "Functional expression cloning of Nanog, a pluripotency sustaining factor in embryonic stem cells," *Cell* 113:643-55 (2003).

Cheng, L. et al., "Properties of four human embryonic stem cell lines maintained in a feeder-free culture system," *Stem Cells* 21:131-42 (2003).

Corrick, C. et al., "Construction of a mouse blastocyst cDNA library by PCR amplification from total RNA," *Mol. Reprod. Dev.* 43:7-16 (1996).

Dang, S. et al., "Controlled, scalable embryonic stem cell differentiation culture," *Stem Cells* 22(3):275-82 (2004).

Deleersnijder, W. et al., "Isolation of markers for chondro-osteogenic differentiation using cDNA library subtraction. Molecular cloning and characterization of a gene belonging to a novel multigene family of integral membrane proteins," *J. Biol. Chem.* 271:19475-82 (1996).

Denning, C. et al., "Common culture conditions for maintenance and cardiomyocyte differentiation of the human embryonic stem cell lines, BG01 and HUES-7," *Int. J. Dev. Biol.* 50:27-37 (2006).

Dravid, G. et al., "Defining the role of Wnt/beta-catenin signaling in the survival, proliferation, and self-renewal of human embryonic stem cells," *Stem Cells* 23(10):1489-501 (2005).

Drukker, M. et al., "Genetic manipulation of human embryonic stem cells," *Human Embryonic Stem Cells*, Chiu & Rao, Eds., Humana Press, Inc., Totowa, NJ, pp. 265-284 (2003).

Dvorak, P. et al., "Expression and potential role of fibroblast growth factor 2 and its receptors in human embryonic stem cells," *Stem Cells* 23:1200-11 (2005).

Eiges, R. et al., "Establishment of human embryonic stem cell-transfected clones carrying a marker for undifferentiated cells," *Curr. Biol.* 11:514-8 (2001).

Eisen, M., "Cluster analysis and display of genome-wide expression patterns," *Proc. Natl. Acad. Sci. USA* 95:14863-8 (1998).

Evans, M. & Kaufman, M., "Establishment in culture of pluripotential cells from mouse embryos," *Nature* 292:154-6 (1981).

Fabb, S. & Ragoussis, J., "High-efficiency human B-cell cloning using hygromycin B-resistant feeder cells," *Biotechniques* 22(5):814-6, 820, 822 (1997).

Fenderson, B. & Andrews, P., "Carbohydrate antigens of embryonal carcinoma cells: changes upon differentiation," *APMIS Suppl.* 27:109-18 (1992).

Finley, M. et al., "Synapse formation and establishment of neuronal polarity by P19 embryonic carcinoma cells and embryonic stem cells," *J. Neurosci.* 16:1056-65 (1996).

Fok, E. et al., "Shear-controlled single-step mouse embryonic stem cell expansion and embryoid body-based differentiation," *Stem Cells* 23(9):1333-42 (2005).

Gao, D. et al., "Structure and transcription of the gene for translation elongation factor 1 subunit alpha of zebrafish (*Danio rerio*)," *Biochim. Biophys. Acta* 1350:1-5 (1997).

Gardner, D. et al., "Culture and transfer of human blastocysts increases implantation rates and reduces the need for multiple embryo transfers," *Fertil. Steril.* 69:84-8 (1998).

Genbacev, O. et al., "Serum-free derivation of human embryonic stem cell lines on human placental fibroblast feeders," *Fertil. Steril.* 83(5):1517-29 (2005).

Gendall, A. et al., "Serum-free derivation of human embryonic stem cell lines on human placental fibroblast feeders," *Int. J. Biochem. Cell. Biol.* 29:829-40 (1997).

Gendron, R. et al., "Induction of embryonic vasculogenesis by bFGF and LIF in vitro and in vivo," *Dev. Biol.* 177:332-46 (1996).

Gerecht-Nir, S. et al., "Bioreactor cultivation enhances the efficiency of human embryoid body (hEB) formation and differentiation," *Biotechnol. Bioeng.* 86(5):493-502 (2004).

GibcoBrl Life Technologies Catalog and Ref. Guide, pp. 1-2 to 1-4, 1-94 and 1-95 (1993).

Gropp, M. et al., "Stable genetic modification of human embryonic stem cells by lentiviral vectors," *Mol. Ther.* 7(2): 281-7 (2003).

Hamaguchi, I. et al., "Lentivirus vector gene expression during ES cell-derived hematopoietic development in vitro," *J. Virol.* 74(22):10778-84 (2000).

Herszfeld, D. et al., "CD30 is a survival factor and a biomarker for transformed human pluripotent stem cells," Nature Biotechnol. 24(3):351-7 (2006).

Hong, Y. et al., "Pluripotency and differentiation of embryonic stem cell lines from the medakafish (*Oryzias latipes*)," *Mech. Dev.* 60: 33-44 (1996).

Hovatta, O. et al., "A culture system using human foreskin fibroblasts as feeder cells allows production of human embryonic stem cells," *Hum. Reprod.* 18:1404-9 (2003).

Itoh, M. et al., "Automated filtration-based high-throughput plasmid preparation system," *Genome Res.* 9:463-70 (1999).

Itskovitz-Eldor, J. et al., "Differentiation of human embryonic stem cells into embryoid bodies compromising the three embryonic germ layers," *Mol. Med.* 6(2):88-95 (2000).

James, D. et al., "TGFbeta/activin/nodal signaling is necessary for the maintenance of pluripotency in human embryonic stem cells," *Development* 132(6):1273-82 (2005).

Johnson, K. et al., "Transgenic mice for the preparation of hygromycin-resistant primary embryonic fibroblast feeder layers for embryonic stem cell selections," *Nucl. Acids Res.* 23(7):1273-5 (1995).

Keirstead, H. et al., "Human embryonic stem cell-derived oligodendrocyte progenitor cell transplants remyelinate and restore locomotion after spinal cord injury," *J. Neurosci.* 25(19):4694-705 (2005).

Keller, G., "In Vitro Differentiation of Embryonic Stem Cells," *Cell Biol.* 7:862-9 (1995).

Kelly, D. & Rizzino, A., "DNA microarray analyses of genes regulated during the differentiation of embryonic stem cells," *Mol. Reprod. Dev.* 56:113-23 (2000).

Klimanskaya, I. et al., "Human embryonic stem cells derived without feeder cells," *Lancet* 365(9471):1636-41 (2005).

Ko, M. et al., "Large-scale cDNA analysis reveals phased gene expression patterns during preimplantation mouse development," *Development* 127:1737-49 (2000).

Koshimizu, U. et al., "Functional requirement of gp130-mediated signaling for growth and survival of mouse primordial germ cells in vitro and derivation of embryonic germ (EG) cells," *Development* 122:1235-42 (1996).

Koshimizu, U. et al., "Retinoic acid is a potent growth activator of mouse primordial germ cells in vitro," *Dev. Biol.* 168:683-5 (1995).

Kuang, W. et al., "Disruption of the lama2 gene in embryonic stem cells: laminin alpha 2 is necessary for sustenance of mature muscle cells," *Exp. Cell Res.* 241:117-25 (1998).

Lebkowski, J. et al., "Human embryonic stem cells: culture, differentiation, and genetic modification for regenerative medicine applications," *Cancer J.* (Suppl. 2):S83-S94 (2001).

Levenstein, M. et al., "Basic fibroblast growth factor support of human embryonic stem cell self-renewal," *Stem Cells* 24(3):568-74 (2006).

Li, M., "Generation of purified neural precursors from embryonic stem cells by lineage selection," *Curr. Biol.* 8:971-4 (1998).

Li, Y. et al., "Expansion of human embryonic stem cells in defined serum-free medium devoid of animal-derived products," *Biotechnol. Bioeng.* 91(6):688-98 (2005).

Lim, J. et al., "Proteosome analysis of conditioned medium from mouse embryonic fibroblast feeder layers which support the growth of human embryonic stem cells," *Proteomics* 2:1187-203 (2002).

Lu, M. et al., "Retrovirus-mediated gene expression in hematopoietic cells correlates inversely with growth factor stimulation," *Hum. Gene Ther.* 7:2263-71 (1996).

Ludwig, T. et al., "Derivation of human embryonic stem cells in defined conditions," *Nat. Biotechnol.* 24(2):185-7 (2006).

Ma, Y. et al., "High-level sustained transgene expression in human embryonic stem cells using lentiviral vectors," *Stem Cells* 21:111-7 (2003).

Mao, M. et al., "Identification of genes expressed in human CD34+ hematopoietic stem progenitor cells by expressed sequence tags and efficient full-length cDNA cloning," *Proc. Natl. Acad. Sci. USA* 95:8175-80 (1998).

Matsuda, T. et al., "STAT3 activation is sufficient to maintain an undifferentiated state of mouse embryonic stem cells," *EMBO J.* 18:4261-9 (1999).

Matsui, Y. et al., "Derivation of pluripotential embryonic stem cells from murine primordial germ cells in culture," *Cell* 70:841-7 (1992).

Mitsui, K. et al., "The homeoprotein Nanog is required for maintenance of pluripotency in mouse epiblast and ES cells," *Cell* 113:631-42 (2003).

Miyamoto, K. et al., "Human placenta feeder layers support undifferentiated growth of primate embryonic stem cells," *Stem Cells* 22:433-40 (2004).

Nichols, J. et al., "Derivation of germline competent embryonic stem cells with a combination of interleukin-6 and soluble interleukin-6 receptor," *Exp. Cell Res.* 215:237-9 (1994).

Nichols, J. et al., "Establishment of germ-line-competent embryonic stem (ES) cells using differentiation inhibiting activity," *Development* 110:1341-8 (1990).

O'Shea, K., "Embryonic stem cell models of development," *Anat. Rec. (New Anat.)* 257(1):32-41 (1990).

Pease, S. et al., "Isolation of embryonic stem (ES) cells in media supplemented with recombinant leukemia inhibitory factor (LIF)," *Dev. Biol.* 141:344-52 (1990).

Pebay, A. et al., "Essential roles of sphingosine-1-phosphate and platelet-derived growth factor in the maintenance of human embryonic stem cells," *Stem Cells* 23(10):1541-8 (2005).

Pedersen, R., "Embryonic stem cells for medicine," *Sci. Amer.* 280(4):69-73 (Apr. 1999).

Pedersen, R., "Studies of in vitro differentiation with embryonic stem cells," *Reprod. Fertil. Dev.* 6:543-52 (1994).

Pera, M. et al., "Human embryonic stem cells," *J. Cell Sci.* 113(Pt. 1):5-10 (2000).

Pera, M., "Human pluripotent stem cells: a progress report," *Curr. Op. Genet. Dev.* 11:595-9 (2001).

Pyle, A. et al., "Neurotrophins mediate human embryonic stem cell survival," *Nat. Biotechnol.* 24(3):344-50 (2006).

Rathjen, J. et al., "Formation of a primitive ectoderm like cell population, EPL cells, from ES cells in response to biologically derived factors," *J. Cell Sci.* 112:601-12 (1999).

Rehman, N. et al., "Development of IVM-IVF produced 8-cell bovine embryos in simple, serum-free media after conditioning or co-culture with buffalo rat liver cells," *Mol. Reprod. Dev.* 38:251-5 (1994).

Reubinoff, B. et al., "Embryonic stem cell lines from human blastocysts: somatic differentiation in vitro," *Nat. Biotechnol.* 18:399-404 (2000).

Richards, M. et al., "Comparative evaluation of various human feeders for prolonged undifferentiated growth of human embryonic stem cells," *Stem Cells* 21:546-56 (2003).

Richards, M. et al., "Human feeders support prolonged undifferentiated growth of human inner cell masses and embryonic stem cells," *Nat. Biotechnol.* 20:933-6 (2002).

Robertson, E., "Derivation and maintenance of embryonic stem cell cultures," *Meth. Mol. Biol.* 75:173-84 (1997).

Rose, T. et al., "Oncostatin M (OSM) inhibits the differentiation of pluripotent embryonic stem cells in vitro," *Cytokine* 6:48-54 (1994).

Rosler, E. et al., "Long-term culture of human embryonic stem cells in feeder-free conditions," *Dev. Dyn.* 229:259-74 (2004).

Sambrook, J. et al., *Molecular Cloning, A Laboratory Manual*, 2nd Edition, CSHL Press, pp. 16.3-16.4, 16.32-16.37 (1989).

Sato, N. et al., "Maintenance of pluripotency in human and mouse embryonic stem cells through activation of Wnt signaling by a pharmacological GSK-3-specific inhibitor," *Nat. Med.* 10(1):55-63 (2004).

Sato, N. et al., "Molecular signature of human embryonic stem cells and its comparison with the mouse," *Dev. Biol.* 260:404-13 (2003).

Schuldiner, M. et al., "Selective ablation of human embryonic stem cells expressing a 'suicide' gene," *Stem Cells* 21:257-65 (2003).

Sciaky, D. et al., "Cultured human fibroblasts express constitutive IL-16 mRNA: cytokine induction of active IL-16 protein synthesis through a caspase-3-dependent mechanism," *J. Immunol.* 164:3806-14 (2000).

Shamblott, M. et al., "Derivation of pluripotent stem cells from cultured human primordial germ cells," *Proc. Natl. Acad. Sci. USA* 95:13726-31 (1998).

Shamblott, M. et al., "Human embryonic germ cell derivatives express a broad range of developmentally distinct markers and proliferate extensively in vitro," *Proc. Natl. Acad. Sci. USA* 98:113-8 (2001).

Simon, C. et al., "First derivation in Spain of human embryonic stem cell lines: use of long-term cryopreserved embryos and animal-free conditions," *Fertil. Steril.* 83:246-9 (2005).

Smith, A. et al., "Buffalo rat liver cells produce a diffusible activity which inhibits the differentiation of murine embryonal carcinoma and embryonic stem cells," *Dev. Biol.* 121:1-9 (1987).

Smith, A. et al., "Inhibition of pluripotential embryonic stem cell differentiation by purified polypeptides," *Nature* 336:688-90 (1988).

Sottile, V. et al., "In vitro osteogenic differentiation of human ES cells," *Cloning Stem Cells* 5(2):149-55 (2003).

Stojkovic, P. et al., "An autogeneic feeder cell system that efficiently supports growth of undifferentiated human embryonic stem cells," *Stem Cells* 23:306-14 (2005).

Takahashi, N. & Ko, M., "Toward a whole cDNA catalog: construction of an equalized cDNA library from mouse embryos," *Genomics* 23:202-10 (1994).

Thomson, J. & Marshall, V., "Primate embryonic stem cells," *Curr. Top. Dev. Biol.* 38:133-65 (1998).

Thomson, J. et al., "Embryonic stem cell lines derived from human blastocysts," *Science* 282:1145-7 (1998).

Thomson, J. et al., "Isolation of a primate embryonic stem cell line," *Proc. Natl. Acad. Sci. USA* 92:7844-8 (1995).

Thomson, J. et al., "Neural differentiation of rhesus embryonic stem cells," *APMIS* 106:149-56 (1998).

Tucker, K. et al., "A transgenic mouse strain expressing four drug-selectable marker genes," *Nucl. Acids Res.* 25(18):3745-6 (1997).

Tucker, R. & Burke, D., "Transgenic mice for the establishment of histidinol-resistant embryonic fibroblast feeder layers," *FASEB J.* 10:1641-5 (1996).

Vallier, L. et al., "Activin/Nodal and FGF pathways cooperate to maintain pluripotency of human embryonic stem cells," *J. Cell Sci.* 118(Pt. 19):4495-509 (2005).

Vallier, L. et al., "Nodal inhibits differentiation of human embryonic stem cells along the neuroectodermal default pathway," *Dev. Biol.* 275:403-21 (2004).

Vassilieva, S. et al., "Establishment of SSEA-1- and Oct-4-expressing rat embryonic stem-like cell lines and effects of cytokines of the IL-6 family on clonal growth," *Exp. Cell Res.* 258:361-73 (2000).

Verfaillie, C. et al., "Stem Cells: Hype and Reality," *Hematology Am. Soc. Hematol. Educ. Program* (2002), pp. 369-391.

Wang, G. et al., "Noggin and bFGF cooperate to maintain the pluripotency of human embryonic stem cells in the absence of feeder layers," *Biochem. Biophys. Res. Commun.* 330:934-42 (2005).

Wang, L. et al., "Human embryonic stem cells maintained in the absence of mouse embryonic fibroblasts or conditioned media are capable of hematopoietic development," *Blood* 105(12):4598-603 (2005).

Wang, Q. et al., "Derivation and growing human embryonic stem cells on feeders derived from themselves," *Stem Cells* 23(9):1221-7 (2005).

Wenk, J. et al., "Glycolipids of germ cell tumors: extended globo-series glycolipids are a hallmark of human embryonal carcinoma cells," *Intl. J. Cancer* 58:108-15 (1994).

Wiles, M. et al., "Embryonic stem cell development in a chemically defined medium," *Exp. Cell Res.* 247:241-8 (1999).

Williams, R. et al., "Myeloid leukaemia inhibitory factor maintains the developmental potential of embryonic stem cells," *Nature* 336:684-7 (1988).

Woltjen, K. et al., "Retro-recombination screening of a mouse embryonic stem cell genomic library," *Nucl. Acids Res.* 28:E41 (2000).

Worrall, D. et al., "A carrot leucine-rich-repeat protein that inhibits ice recrystallization," *Science* 282:115-7 (1998).

Xiong, J. et al., "Large-scale screening for developmental genes in embryonic stem cells and embryoid bodies using retroviral entrapment vectors," *Dev. Dyn.* 212:181-97 (1998).

Xu, C. et al., "Basic fibroblast growth factor supports undifferentiated human embryonic stem cell growth without conditioned medium," *Stem Cells* 23(3):315-23 (2005).

Xu, C. et al., "Characterization and enrichment of cardiomyocytes derived from human embryonic stem cells," *Circ. Res.* 91(6):501-8 (2002).

Xu, C. et al., "Feeder-free growth of undifferentiated human embryonic stem cells," *Nature Biotech.* 19:971-4 (2001).

Xu, C. et al., "Immortalized fibroblast-like cells derived from human embryonic stem cells support undifferentiated cell growth," *Stem Cells* 22:972-80 (2004).

Xu, R. et al., "Large-scale screening for developmental genes in embryonic stem cells and embryoid bodies using retroviral entrapment vectors," *Nat. Methods* 2(3):185-90 (2005).

Yu, H. et al., "Heterogeneous populations of ES cells in the generation of a floxed presenilin-1 allele," *Genesis* 26:5-8 (2000).

Zandstra, P. et al., "Leukemia inhibitory factor (LIF) concentration modulates embryonic stem cell self-renewal and differentiation independently of proliferation," *Biotechnol. Bioeng.* 69:607-17 (2000).

Zhang, S-C. et al., "In vitro differentiation of transplantable neural precursors from human embryonic stem cells," *Nat. Biotechnol.* 19:1129-33 (2001).

Zwaka, T. & Thomson, J., "Homologous recombination in human embryonic stem cells," *Nat. Biotechnol.* 21:319-21 (2003).

"Poultry: Reproduction & Incubation, Stages in chick embryo development", *Web pages from* http://muscares.com/poultry/reproductions/poultry_chicks_embryo.html (Dec. 8, 2010), 2 pages.

Froud, S., "The develpment, benefits and disadvantages of serum-free media", *Dev. Biol. Stand.* 99 (1999), pp. 157-166.

Kehoe, D. et al., "Scalable stirred-suspension bioreactor culture of human pluripotent stem cells", *Tissue Eng.* 16(2), Part A, pp. 405-421.

Leist, C. et al., "Potential and problems of animal cells in suspension culture", *J. Biotech.* 15(1-2) (1990), pp. 1-46.

Merten, O.-W., "Safety issues of Animal Products Used in Serum-Free Media", *Dev. Biol. Stand.* 99 (1999), pp. 167-180.

Oh, S. et al., "Human embryonic stem cells: technological challenges towards therapy", *Clin. Exp. Pharmacol. Physiol.* 33 (2006), pp. 489-495.

Schubeler, D. et al., "Scaffold/matrix-attached regions act upon transcription in a context-dependent manner", *Biochemistry* 35 (1996), pp. 11160-9.

Stojkovic, M. et al., "Derivation, growth and applications of human embryonic stem cells", *Reproduction* 128 (2004), pp. 259-267.

Ornitz, D. et al., "Fibroblast growth factors", *Genome Biol.* 2(3), (2001), pp. 1-12.

Xiao, L. et al., "Activin A maintains self-renewal and regulates fibroblast growth factor, Wnt, and bone morphogenetic protein pathways in human embryonic stem cells," *Stem Cells* 24, (2006), pp. 1476-1486.

\* cited by examiner

MEF-CM bFGF-high bFGF-low bFGF + SCF bFGF + Flt-3L

MICRO-CARRIER CULTURE SYSTEM FOR RAPID EXPANSION OF HUMAN EMBRYONIC STEM CELLS

REFERENCE TO RELATED APPLICATIONS

This application is a continuation of U.S. application Ser. No. 12/170,219, filed Feb. 22, 2010, which is a continuation of U.S. application No. 12/170,219, filed Jul. 9, 2008, which claims priority to U.S. Ser. No. 10/330,873, filed Dec. 24, 2002, now U.S. Pat. No. 7,413,902, which is a continuation of U.S. 09/530,346, filed Aug. 29, 2000, now U.S. Pat. No. 6,800,480, which claims priority to PCT/US98/22619. This application is also a continuation of U.S. Ser. No. 10/235,094, filed Sep. 4, 2002, now U.S. Pat. No. 7,410,798, which claims priority to provisional application U.S. 60/317,478, filed Sep. 5, 2001 and PCT/US01/01030, filed Jan. 10, 2001, which claims priority to U.S.Provisional Application Nos. 60/175, 581 filed Jan. 11, 2000 and 60/213,739 filed Jun. 22, 2000, all of which are hereby incorporated by reference.

TECHNICAL FIELD

This invention relates generally to the field of cell biology of embryonic cells. More specifically, it relates to the propagation of pluripotent stem cells, and culture conditions and materials that facilitate propagation and use of human embryonic stem cells.

BACKGROUND

Considerable interest has been generated in the field of regenerative medicine by recent work relating to the isolation and propagation of human stem cells from the early embryo. These cells have two very special properties: First, unlike other normal mammalian cell types, they can be propagated in culture almost indefinitely, providing a virtually unlimited supply. Second, they can be used to generate a variety of tissue types of interest as a source of replacement cells and tissues that are damaged in the course of disease, infection, or because of congenital abnormalities.

Early work on pluripotent stem cells was done in mice (Robertson, Meth. Cell Biol. 75:173, 1997; and Pedersen, Reprod. Fertil. Dev. 6:543, 1994). Experiments with human stem cells have required overcoming a number of additional technical difficulties and compilations. As a result, technology for culturing and differentiating human pluripotent stem cells is considerably less advanced.

Thomson et al. (U.S. Pat. No. 5,843,780; Proc. Natl. Acad. Sci. USA 92:7844, 1995) were the first to successfully isolate and propagate pluripotent stem cells from primates. They subsequently derived human embryonic stem (hES) cell lines from human blastocysts (Science 282:114, 1998). Gearhart and coworkers derived human embryonic germ (hEG) cell lines from fetal gonadal tissue (Shamblott et al., Proc. Natl. Acad. Sci. USA 95:13726, 1998; and U.S. Pat. No. 6,090, 622). Both hES and hEG cells have the long-sought characteristics of pluripotent stem cells: they can be cultured extensively without differentiating, they have a normal karyotype, and they remain capable of producing a number of important cell types.

A significant challenge to the use of pluripotent stem cells for therapy is that they are traditionally cultured on a layer of feeder cells to prevent differentiation (U.S. Pat. Nos. 5,843, 780; 6,090,622). According to Thomson et al. (Science 282: 114, 1998), hPS cells cultured without feeders soon die, or differentiate into a heterogeneous population of committed cells. Leukemia inhibitory factor (LIF) inhibits differentiation of mouse ES cells, but it does not replace the role of feeder cells in preventing differentiation of human ES cells.

International Patent Publication WO 99/20741 (Geron Corp.) is entitled Methods and materials for the growth of primate-derived primordial stem cells. A cell culture medium is described for growing primate-derived primordial stem cells in a substantially undifferentiated state, having a low osmotic pressure and low endotoxin levels. The basic medium can be combined with a serum effective to support the growth of primate-derived primordial stem cells on a substrate of feeder cells or a feeder cell matrix. The medium may also include non-essential amino acids, an anti-oxidant, and growth factors that are either nucleosides or a pyruvate salt.

International Patent Publication WO 01/51616 (Geron Corp.) is entitled Techniques for growth and differentiation of human pluripotent stem cells. An article by Xu et al. (Nature Biotechnology 19:971, 2001) is entitled Feeder-free growth of undifferentiated human embryonic stem cells. An article by Lebkowski et al. (Cancer J. 7 Suppl. 2:S83, 2001) is entitled Human embryonic stem cells: culture, differentiation, and genetic modification for regenerative medicine applications. These publications report exemplary culture methods for propagating human embryonic stem cells in an undifferentiated state, and their use in preparing cells for human therapy.

New technology to facilitate growing and manipulating undifferentiated pluripotent stem cells would be a substantial achievement towards realizing the full commercial potential of embryonic cell therapy.

SUMMARY OF THE INVENTION

This disclosure provides an improved system for expanding primate pluripotent stem (pPS) cells. The technology allows the user to rapidly produce high-quality pPS cells for use in therapy are drug discovery, free of undesired contamination by cells of other species and other tissue types.

Application of the technology involves introducing stem cells into a culture environment containing components described and exemplified in more detail in the sections that follow. Typically, the environment will contain a support structure, a culture medium, and one or more factors added to the medium that support proliferation of the pPS cells in an undifferentiated state. Exemplary support structures are made from isolated extracellular matrix components. Exemplary culture media comprise an isotonic buffer, a protein or amino acid source, and may also comprise nucleotides, lipids, and hormones. An exemplary factor for adding to the medium is a fibroblast growth factor. It has been discovered that sufficient FGF in a suitable medium is sufficient to maintain pPS cells in a substantially undifferentiated state through extended culture. Other factors listed in this disclosure can be added to improve the quality and expansion rate of the culture when desired.

The culture environment can be essentially free of feeder cells, since feeder cells are not required to keep the pPS cells proliferating in an undifferentiated state. In this embodiment, the cells consist essentially of undifferentiated pPS cells, and progeny thereof that may have begun differentiation or adopted an altered phenotype. Since they are all derived from the same pPS cells, all of the cells in the culture will have the same genotype, which means that the cells have the same chromosomal DNA (plus or minus karyotype abnormalities or deliberate genetic alterations). This can be ascertained by demonstrating that essentially all the cells in the culture are derived from the same pPS cells. Included are mixed populations made by combining different lines of pPS cells and their progeny, as long as essentially each of the cells in the culture are progeny of one of the starting cell lines.

An important virtue of this system is that there is no need to condition the medium before combining it with the stem cells. The skilled reader may wish to precondition the medium with other cell lines in advance, but the medium can be added "fresh" to the pPS cells and still support proliferation without differentiation. This means that the medium has not been cultured with other cell types before being added to the pPS cell culture (either by direct substitution for spent medium, or in a gradual or continuous exchange system).

Another virtue of the system is the ability to adjust conditions so that the cells expand more rapidly (as much as 1½ times faster) than they do when cultured on feeder cells according to traditional techniques, or in conditioned medium. While the user need not expand the cells rapidly in order to use this invention, she has the option of growing the cells with a doubling time of as little as 24 hours.

Using this culture system (optionally passaging the cells into new culture environments when required), populations of pluripotent stem cells can be obtained that are expanded 10-fold or more when compared with the starting population. Even after expansion, a high proportion of the cells are still undifferentiated, according to morphological characteristics, phenotypic markers, or the ability to differentiate into derivatives of the three embryonic germ layers (endoderm, mesoderm, and ectoderm).

Embodiments of this invention include the culture environment in which the pPS cells are expanded and its use, the combined composition of the environment and the pPS cells, and various methods for expanding pPS cells using the reagents and techniques described in this disclosure. This system can be used with pPS cells of various types, exemplified by cells isolated or propagated from human blastocysts, such as established human embryonic stem cell lines and their equivalents.

This system can be used to generate genetically altered pPS cells. The cells are transfected with a suitable vector for effecting the desired genetic alteration, such as a DNA-lipid complex. This is facilitated in the feeder-free culture systems of this invention. The genetically altered cell population can be expanded as already described, before or after genetic alteration and/or selection of the altered genotype.

This system can also be used to generate differentiated cell types of various kinds. After the undifferentiated pPS cells are expanded to the desired number, they are caused to differentiate according to any of a variety of differentiation paradigms provided later in this disclosure. Differentiated populations can be obtained in which at least 95% of the cells represent the same tissue type or germ layer: for example, neural cells, hepatocytes, cardiomyocytes, mesenchymal cells, or osteoblasts.

These and other aspects of the invention will be apparent from the description that follows.

DRAWINGS

FIG. 1 shows the morphology of hES cells in feeder-free culture. Panel A (Left Side) shows morphology of hES cells cultured on feeder cells in regular culture medium (mEF/RM), or on Matrigel®, laminin, fibronectin, or collagen IV in mEF conditioned medium. Panel B (Right Side) shows morphology of hES cells maintained on Matrigel® in medium conditioned by mEF, NHG190, STO and BJ 5Ta cells, compared with unconditioned regular medium (RM). hES cells cultured in suitable conditioned media contained colonies with appropriate morphology for undifferentiated cells.

Figure 2:
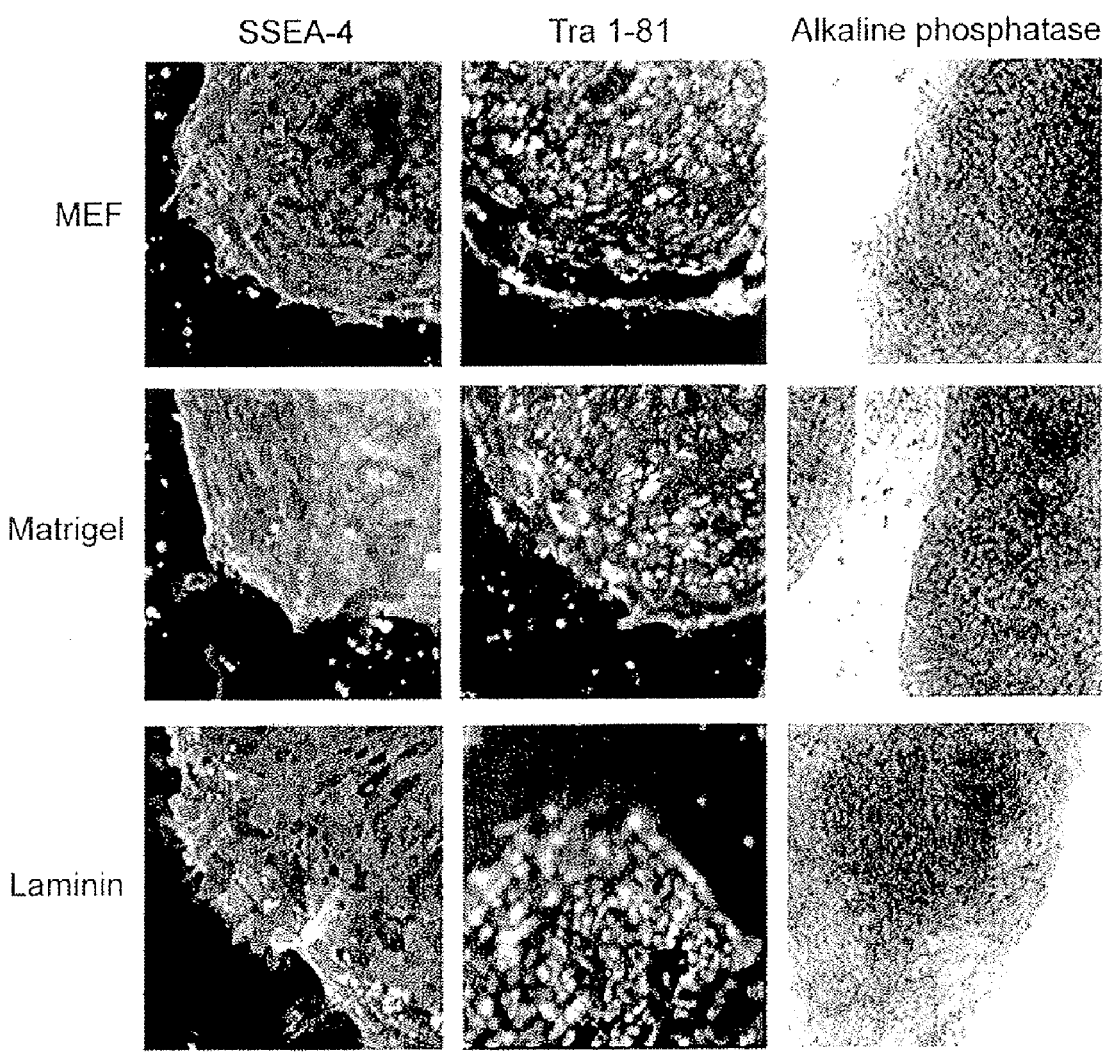

FIG. 2 shows marker expression detected by immunocytochemistry for cells grown with primary feeder cells (mEF) or on the extracellular matrices Matrigel® or laminin in conditioned medium.

Figure 3:
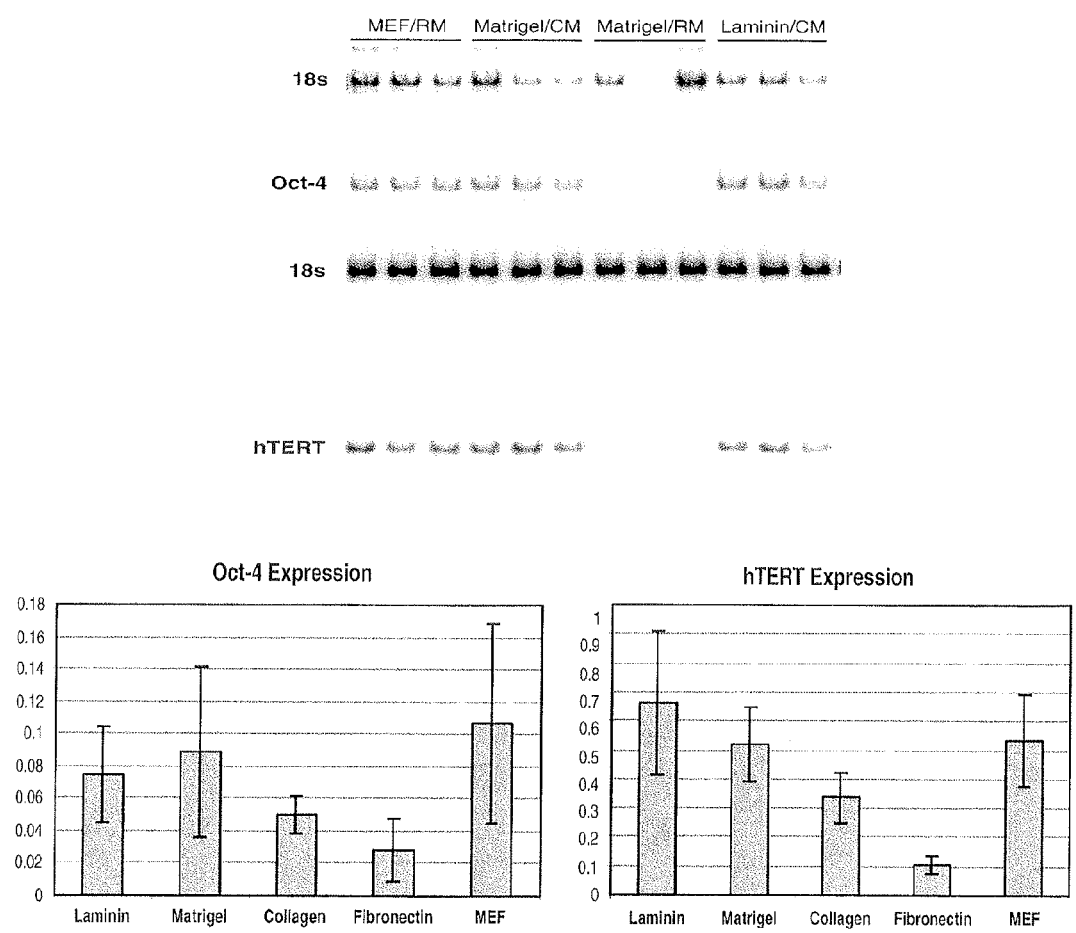

FIG. 3 provides an analysis of OCT-4 and hTERT expression in hES cells cultured with feeder cells (mEF) or extracellular matrix (Matrigel® or laminin) with regular medium (RM) or conditioned medium (CM). The upper panel shows OCT-4 and hTERT expression at the mRNA level by RT-PCR. The lower panel compares the level of expression for cells grown on different substrates, expressed as the ratio of OCT-4 or hTERT to the 18s standard.

Figure 4:
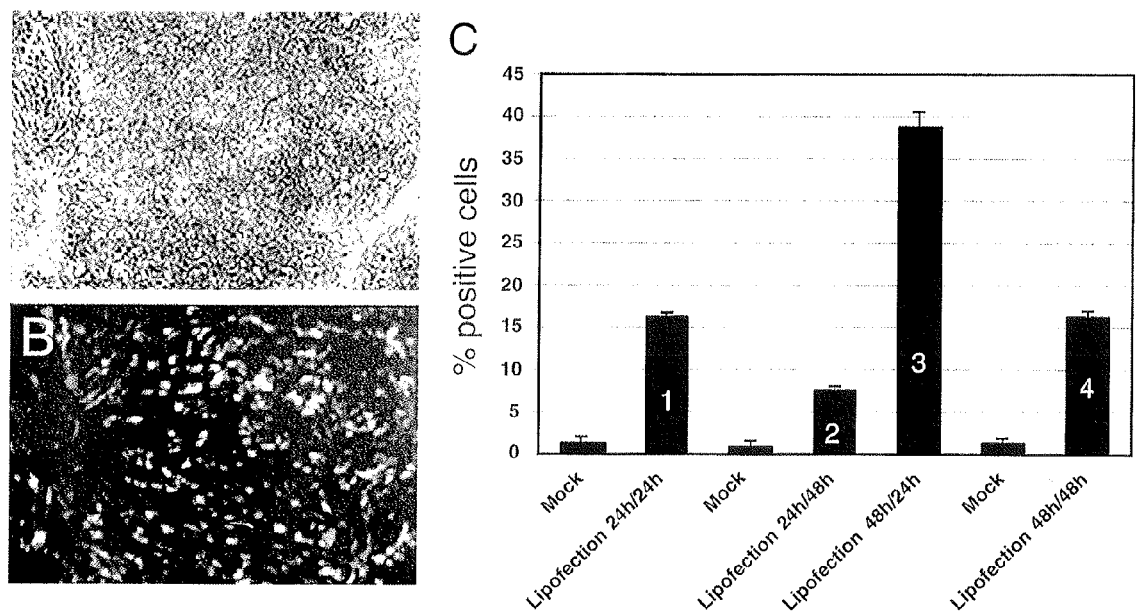

FIG. 4 is from an experiment in which hES were genetically altered in feeder-free culture by lipofection. Panel A shows morphology of hES cells on laminin after they have been transfected for GFP expression. Panel B shows GFP expression in the same colony. Panel C shows percentage of cells expressing GFP under various conditions. Bright green cells were observed in undifferentiated hES colonies of feeder-free cultures. In contrast, very few green cells were found in hES cell colonies grown on feeders.

Figure 5:
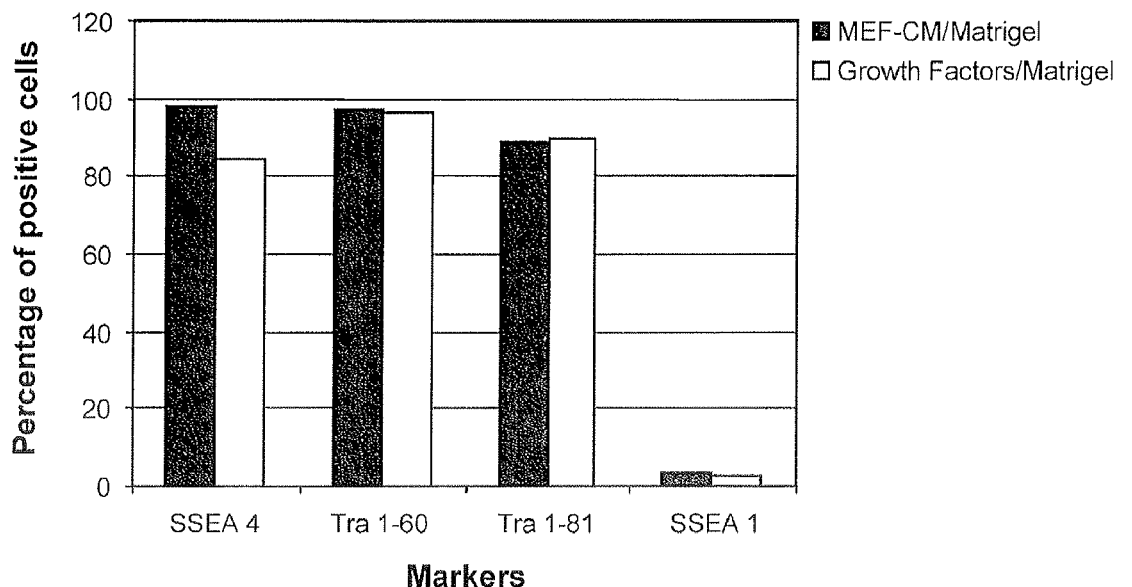
Figure 5:
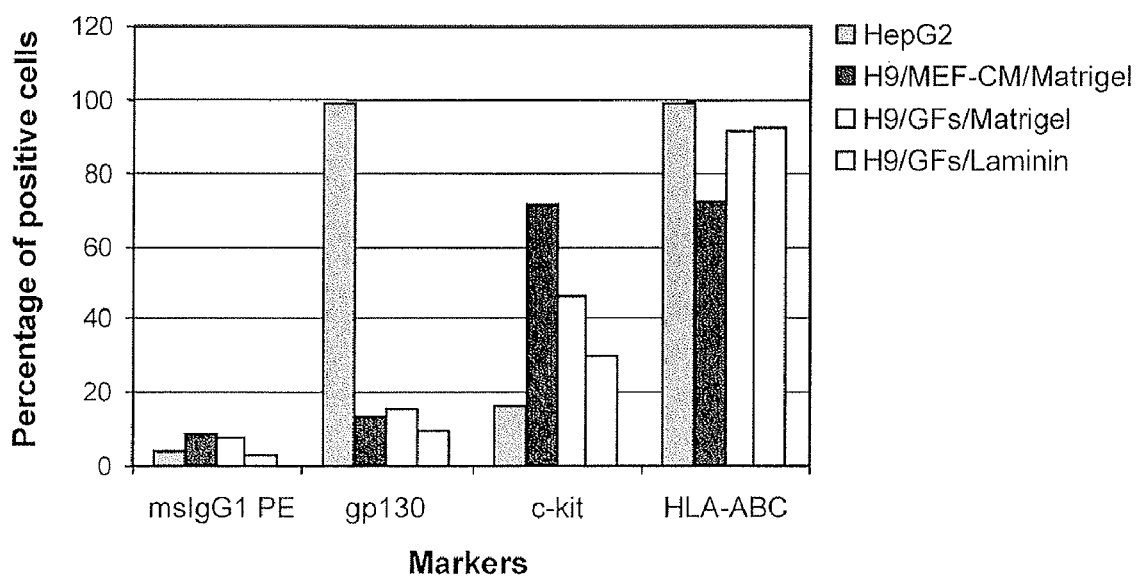

FIG. 5 shows FACS analysis for phenotypic markers on hES cells grown in various culture environments. The H9 cell line was maintained in a fresh (unconditioned) medium containing basic fibroblast growth factor, stem cell factor (c-kit ligand), and other factors that bind to receptors associated with gp130. The levels of SSEA-1, SSEA-4, Tra 1-60 and Tra 1-81 (characteristic of undifferentiated hES cells) were similar to cells maintained in medium conditioned by mouse embryonic fibroblasts (MEF-CM). The cultured cells expressed c-kit (a receptor for stem cell factor), but not gp130 (associated with the LIF receptor). These cells can still produce derivatives of all three embryonic germ layers.

Figure 6:
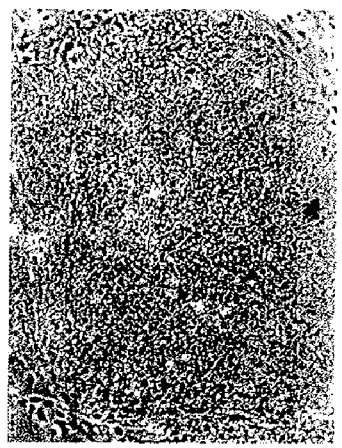
Figure 6:
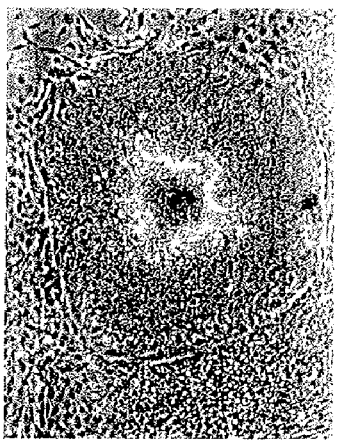
Figure 6:
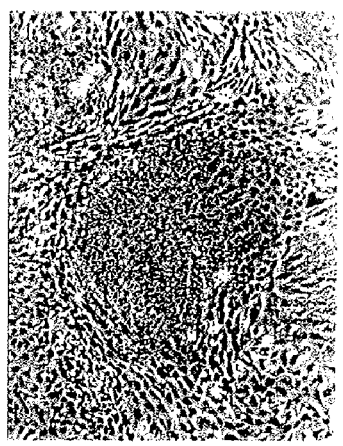
Figure 6:
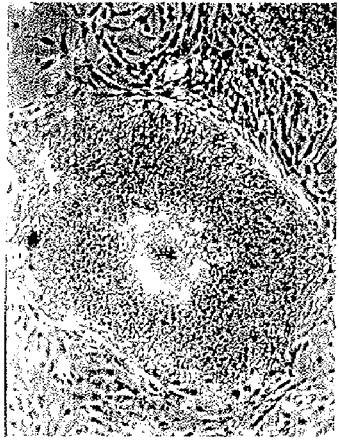
Figure 6:
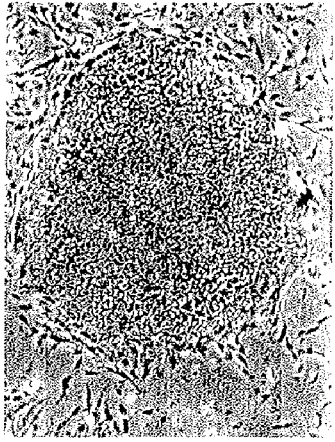

FIG. 6 shows colonies of undifferentiated hES cells growing in fresh ES medium containing basic fibroblast growth factor alone at high (40 ng/mL) or low (8 ng/mL) concentration, or bFGF (40 ng/mL) in combination with SCF (15 ng/mL) or Flt-3 ligand (75 ng/mL). Shown for comparison are hES cells growing in ES medium condoned by irradiated mouse embryonic fibroblasts. It has been discovered that bFGF at concentrations of 40 ng/mL is sufficient to maintain the hES cells in an undifferentiated form. The presence of SCF or Flt-3 ligand under certain circumstances can improve the proportion of undifferentiated cells in the culture.

Figure 7:
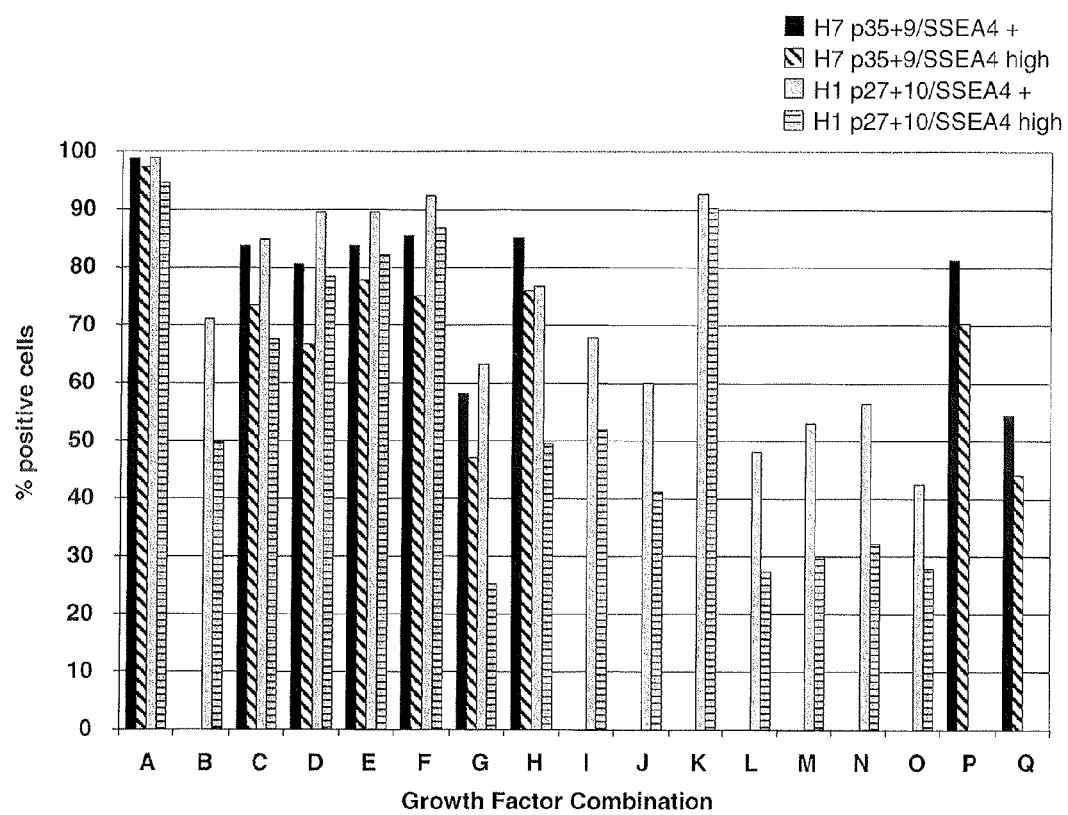

FIG. 7 shows expression of SSEA-4 as evaluated by FACS analysis in various growth factor combinations, described in Example 6.

Figure 8:
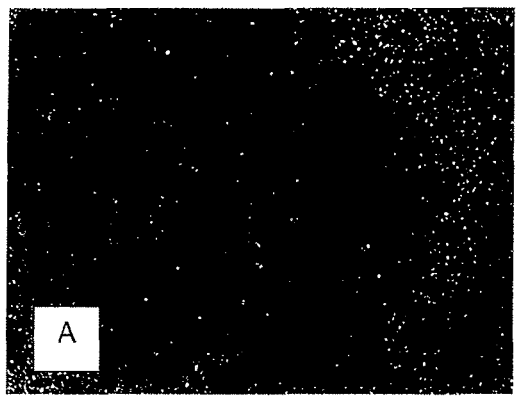
Figure 8:
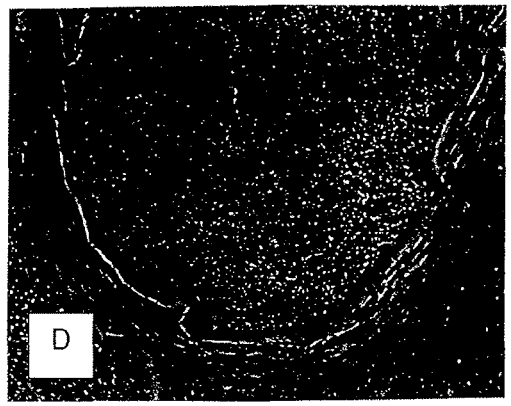
Figure 8:
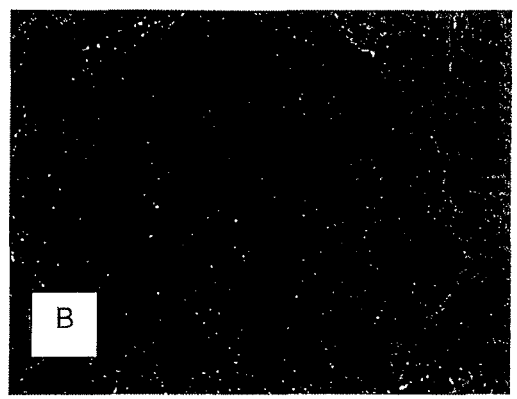
Figure 8:
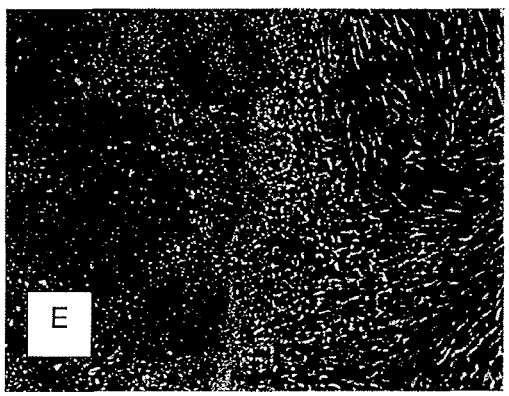
Figure 8:
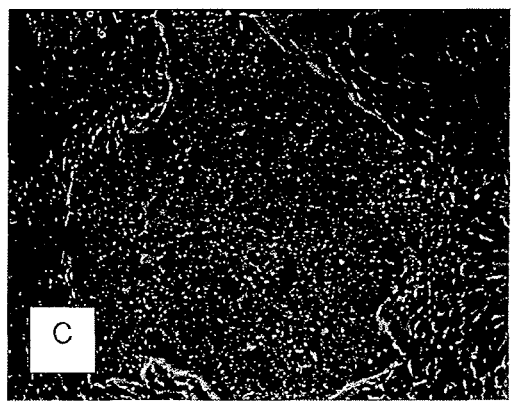

FIG. 8 shows colonies of hES cells after 6 passages (sufficient for full adaptation) in different base media. (A) mEF conditioned ES medium+bFGF (8 ng/mL); (B) X-VIVO™ 10+bFGF (40 ng/mL); (C) X-VIVO™ 10+bFGF (40 ng/mL)+stem cell factor (SCF, Steel factor) (15 ng/mL); (D) X-VIVO™ 10+bFGF (40 ng/mL)+Flt3 ligand (75 ng/mL); (E) QBSF™-60+bFGF (40 ng/mL). All three base media (ES medium, X-VIVO™ 10, and QBSF™-60) can be used to expand hES cells in feeder-free culture. In this illustration, the cells growing in combination shown in (C) expanded 8.2-fold per passage, whereas those in conditioned medium expanded 2.2-fold. The use of suitable fresh medium causes rapid expansion of undifferentiated hES cells.

Figure 9:
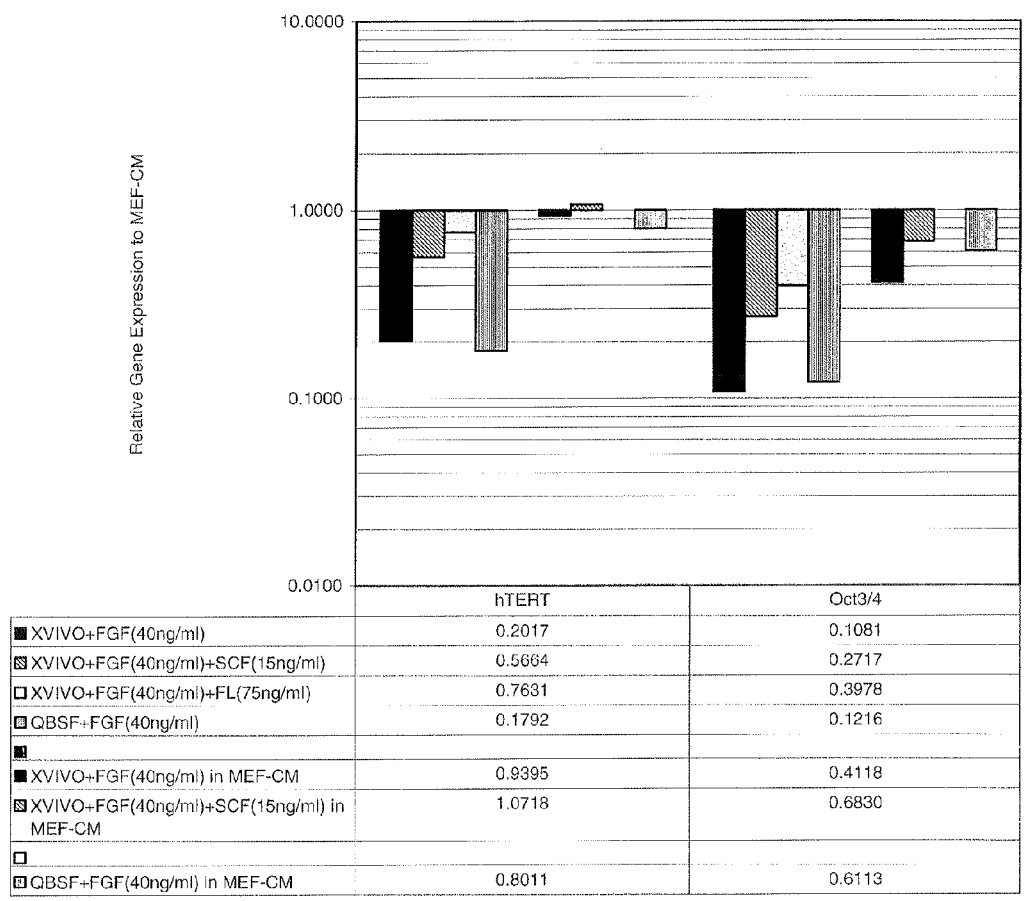

FIG. 9 shows the gene expression profile of hTERT and Oct3/4, measured by real time RT-PCR, as described in Example 8.

Figure 10:
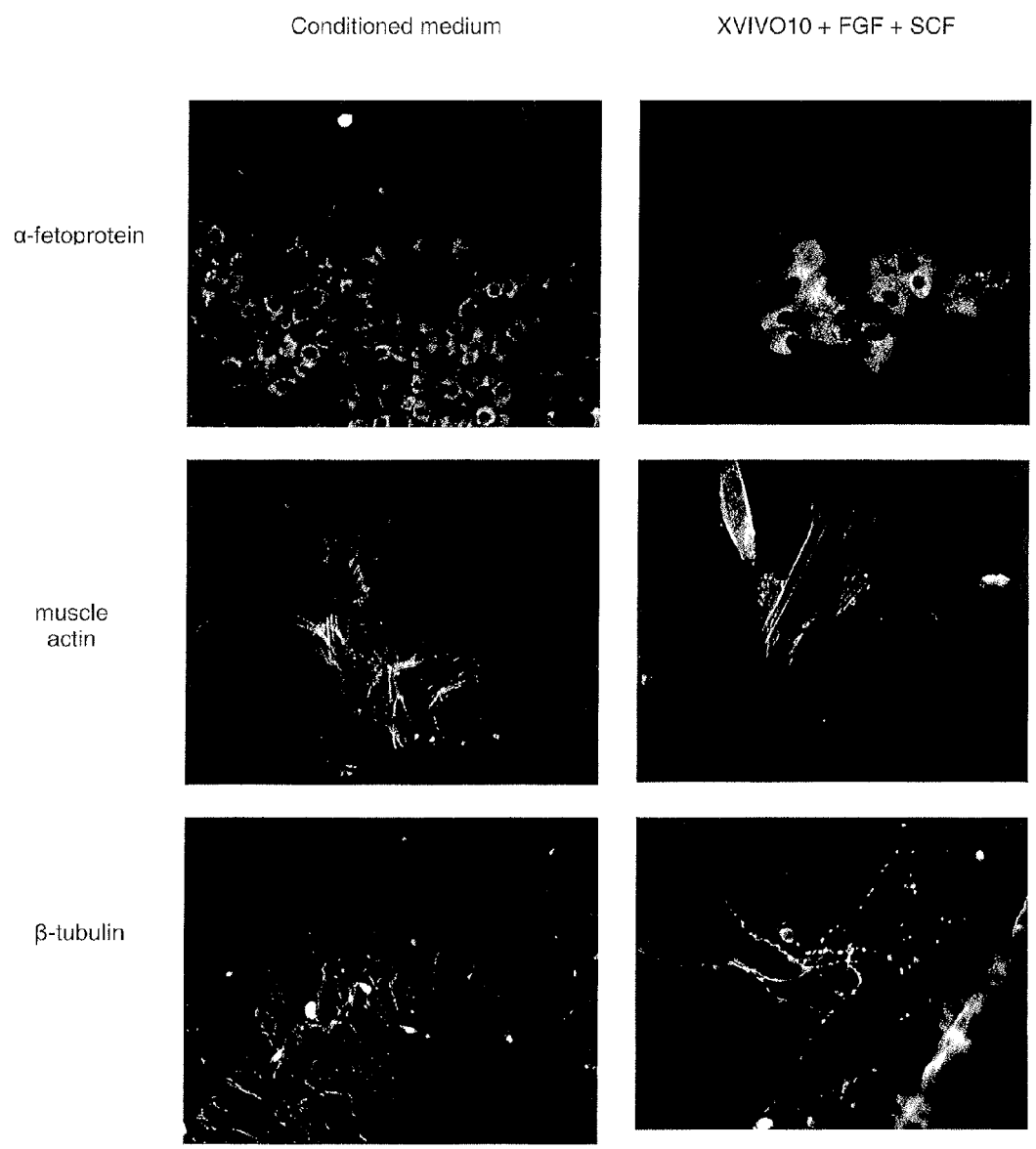

FIG. 10 demonstrates that cells cultured in unconditioned medium retain their pluripotency. hES cells passaged 7 times in mEF conditioned medium, or unconditioned X-VIVO™ 10 medium containing bFGF and SCF. The cells were then differentiated into embryoid bodies, plated, and analyzed by immunocytochemistry for phenotypic markers representing each of the three germ layers. The cells stain for α-fetoprotein (representing ectoderm); muscle actin (representing mesoderm), and β-tubulin III (representing endoderm). The cells grown in the culture system described in this patent application are suitable for making a wide scope of differentiated cell types.

DETAILED DESCRIPTION

Previous technology for culturing primate pluripotent stem (pPS) cells has required that the cell culture environment contain feeder cells in order to prevent them from differentiating. In particular, the standard feeder cells used for culturing human embryonic stem cell are irradiated mouse embryonic fibroblasts. Unfortunately, using feeder cells increases production costs, impairs scale-up, and produces mixed cell populations that complicate quality control and regulatory approval for use in human therapy.

This disclosure provides a system for rapidly expanding primate pluripotent stem (pPS) cells in vitro without requiring a layer of feeder cells to support the culture and inhibit differentiation.

As a result of thorough investigation of the features required, it has now been determined that the beneficial effect of the feeder cells can be replaced by providing a suitable surface and a suitable mixture of soluble factors. It turns out that more intimate interaction between the pPS cells and the feeder cells is not required, as long as the signal transduction pathways required for undifferentiated growth are adequately activated by factors in the culture environment.

In one version of the feeder-free culture system, the pPS cells are grown in medium that has been preconditioned in a separate culture of feeder cells of mouse or human origin (FIG. 1). The feeder cells are grown to confluence in their own culture environment, inactivated, and then cultured in one or more batches of fresh medium to allow them to release an effective combination of factors. The medium is then harvested, and used to support growth of undifferentiated pPS cells plated onto a suitable substrate. Doubling rate is comparable to hES grown on feeder cells. Typically, the medium is changed daily, and the cells are split and passaged every 6 or 7 days.

In an alternative version of the feeder-free culture system, the pPS cells are grown in medium that has not been preconditioned, but has been supplemented with ingredients that perform essentially the same function as factors secreted from feeder cells. Certain factor combinations comprising moderate to high levels of fibroblast growth factors and other cells generate cultures that can proliferate 20-fold or more through 6 or more passages, while maintaining a majority of the cells in the culture in an undifferentiated state (FIGS. 6 and 8). Near confluence, most of the cells have morphological features of undifferentiated cells, and express characteristic phenotypic markers: SSEA-4, Tra-1-60, Tra-1-81, Oct-4, and telomerase reverse transcriptase (TERT).

Quite surprisingly, it was found that pPS cells grown in unconditioned medium expand substantially more rapidly than pPS cells grown on feeder cells or in conditioned medium. The reasons for this are unclear; nor was it predictable based on what was previously known about pPS cell culture. Nevertheless, this finding is important, because it provides a rapid expansion method for producing commercial grade undifferentiated pPS cells on a commercial scale. Now that this technology is available, the production of pPS cells for treating human patients in need of tissue regeneration holds considerable promise.

The techniques provided in this invention represent an important advance in the potential use of pluripotent stem cells for research and therapeutic use. Further advantages of the invention will be understood from the sections that follow.

DEFINITIONS

Prototype "primate Pluripotent Stem cells" (pPS cells) are pluripotent cells derived from pre-embryonic, embryonic, or fetal tissue at any time after fertilization, and have the characteristic of being capable under the right conditions of producing progeny of several different cell types. pPS cells are capable of producing progeny that are derivatives of each of the three germ layers: endoderm, mesoderm, and ectoderm, according to a standard art-accepted test, such as the ability to form a teratoma in a suitable host, or the ability to differentiate into cells stainable for markers representing tissue types of all three germ layers in culture.

Included in the definition of pPS cells are embryonic cells of various types, exemplified by human embryonic stem (hES) cells, defined below; embryonic stem cells from other primates, such as Rhesus or marmoset stem cells (Thomson et al., Proc. Natl. Acad. Sci. USA 92:7844, 1995; Developmental Biology 38:133, 1998); and human embryonic germ (hEG) cells (Shamblott et al., Proc. Natl. Acad. Sci. USA 95:13726, 1998). Other types of pluripotent cells are also included in the term. Any cells of primate origin that are capable of producing progeny that are derivatives of all three germinal layers are included, regardless of whether they were derived from embryonic tissue, fetal tissue, or other sources. It is beneficial to use pPS cells that are karyotypically normal and not derived from a malignant source.

Prototype "human Embryonic Stem cells" (hES cells) are described by Thomson et al. (Science 282:1145, 1998; U.S. Pat. No. 6,200,806). The scope of the term covers pluripotent stem cells that are derived from a human embryo at the blastocyst stage, or before substantial differentiation of the cells into the three germ layers. Those skilled in the art will appreciate that except where explicitly required otherwise, the term includes primary tissue and established lines that bear phenotypic characteristics of hES cells, and derivatives of such lines that still have the capacity of producing progeny of each of the three germ layers.

pPS cell cultures are described as "undifferentiated" or "substantially undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view with high nuclear/cytoplasmic ratios and prominent nucleoli. It is understood that colonies of undifferentiated cells within the population will often be surrounded by neighboring cells that are differentiated. Nevertheless, the undifferentiated colonies persist when the population is cultured or passaged under appropriate conditions, and individual undifferentiated cells constitute a substantial proportion of the cell population. Cultures that are substantially undifferentiated contain at least 20% undifferentiated pPS cells, and may contain at least 40%, 60%, or 80% in order of increasing preference (in terms percentage of cells with the same genotype that are undifferentiated).

Whenever a culture or cell population is referred to in this disclosure as proliferating "without differentiation", what is meant is that after proliferation, the composition is substantially undifferentiated according to the preceding definition. Populations that proliferate through at least four passages (~20 doublings) without differentiation will contain substantially the same proportion of undifferentiated cells (or possibly a higher proportion of undifferentiated cells) when evaluated at the same degree of confluence as the originating culture.

"Feeder cells" or "feeders" are terms used to describe cells of one type that are co-cultured with cells of another type, to provide an environment in which the cells of the second type can grow. pPS cell populations are said to be "essentially free" of feeder cells if the cells have been grown through at least one round after splitting in which fresh feeder cells are not added to support the growth of pPS cells. A feeder free culture will contain less than about ~5% feeder cells. Compositions containing less than 1%, 0.2%, 0.05%, or 0.01% feeder cells (expressed as % of total cells in the culture) are increasingly more preferred.

A "growth environment" is an environment in which cells of interest will proliferate in vitro. Features of the environment include the medium in which the cells are cultured, and a supporting structure (such as a substrate on a solid surface) if present.

A "nutrient medium" is a medium for culturing cells containing nutrients that promote proliferation. The nutrient medium may contain any of the following in an appropriate combination: isotonic saline, buffer, amino acids, serum or serum replacement, and other exogenously added factors.

A "conditioned medium" is prepared by culturing a first population of cells in a medium, and then harvesting the medium. The conditioned medium (along with anything secreted into the medium by the cells) may then be used to support the growth of a second population of cells. Where a particular ingredient or factor is described as having been added to the medium, what is meant is that the factor (or a cell or particle engineered to secrete the factor) has been mixed into the medium by deliberate manipulation.

A "fresh medium" is a medium that has not been purposely conditioned by culturing with a different cell type before being used with the cell type it is ultimately designed to support. Otherwise, no limitations are intended as to its manner of preparation, storage, or use. It is added fresh (by exchange or infusion) into the ultimate culture, where it may be consumed or otherwise processed by the cell types that are present.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. The genetic alteration is said to be "inheritable" if progeny of the altered cell have the same alteration.

The term "antibody" as used in this disclosure refers to both polyclonal and monoclonal antibody of any species. The ambit of the term encompasses not only intact immunoglobulin molecules, but also fragments and genetically engineered derivatives of immunoglobulin molecules and equivalent antigen binding molecules that retain the desired binding specificity.

General Techniques

General methods in molecular genetics and genetic engineering are described in the current editions of *Molecular Cloning: A Laboratory Manual*, (Sambrook et al., Cold Spring Harbor); *Gene Transfer Vectors for Mammalian Cells* (Miller & Calos eds.); and *Current Protocols in Molecular Biology* (F. M. Ausubel et al. eds., Wiley & Sons). Cell biology, protein chemistry, and antibody techniques can be found in *Current Protocols in Protein Science* (J. E. Colligan et al. eds., Wiley & Sons); *Current Protocols in Cell Biology* (J. S. Bonifacino et al., Wiley & Sons) and *Current Protocols in Immunology* (J. E. Colligan et al. eds., Wiley & Sons.). Reagents, cloning vectors, and kits for genetic manipulation referred to in this disclosure are available from commercial vendors such as BioRad, Stratagene, Invitrogen, ClonTech, and Sigma-Aldrich Co.

Cell culture methods are described generally in the current edition of *Culture of Animal Cells: A Manual of Basic Technique* (R. I. Freshney ed., Wiley & Sons); *General Techniques of Cell Culture* (M. A. Harrison & I. F. Rae, Cambridge Univ. Press), and *Embryonic Stem Cells: Methods and Protocols* (K. Turksen ed., Humana Press). Other texts are *Creating a High Performance Culture* (Aroselli, Hu. Res. Dev. Pr. 1996) and *Limits to Growth* (D. H. Meadows et al., Universe Publ. 1974). Tissue culture supplies and reagents are available from commercial vendors such as Gibco/BRL, Nalgene-Nunc International, Sigma Chemical Co., and ICN Biomedicals.

Sources of Pluripotent Stem Cells

Suitable source cells for culturing and differentiation according to this invention include established lines of pluripotent cells derived from tissue formed after gestation. Exemplary primary tissue sources are embryonic tissue (such as a blastocyst), or fetal tissue taken any time during gestation, typically but not necessarily before 10 weeks gestation. Non-limiting exemplars are established lines of primate embryonic stem (ES) cells, exemplified below; and embryonic germ (EG) cells, described in Shamblott et al., Proc. Natl. Acad. Sci. USA 95:13726, 1998; and U.S. Pat. No. 6,090,622. Also contemplated is use of the techniques of this disclosure during the initial establishment or stabilization of such cells, in which case the source cells would be primary pluripotent cells taken directly from the tissues listed.

Establishing Lines of Human Embryonic Stem (hES) Cells

Embryonic stem cells can be isolated from blastocysts of members of the primate species (U.S. Pat. No. 5,843,780; Thomson et al., Proc. Natl. Acad. Sci. USA 92:7844, 1995). Human embryonic stem (hES) cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000. Equivalent cell types to hES cells include their pluripotent derivatives, such as primitive ectoderm-like (EPL) cells, as outlined in WO 01/51610 (Bresagen).

Materials for the preparation of hES cell lines according to traditional methods are as follows. Serum-containing ES medium is made with 80% DMEM (typically knockout DMEM), 20% defined fetal bovine serum (FBS), 1% non-essential amino acids, 1 mM L-glutamine, and 0.1 mM β-mercaptoethanol. The medium is filtered and stored at 4° C. for no longer than 2 weeks. Serum-free ES medium is made with 80% KO DMEM, 20% serum replacement (Gibco #10828-028), 1% non-essential amino acids, 1 mM L-glutamine, and 0.1 mM β-mercaptoethanol. Just before use, human bFGF is added to a final concentration of 4-8 ng/mL.

Mouse embryonic fibroblasts (mEF) for use as feeder cells can be obtained from outbred CF1 mice (SASCO) or other suitable strains. The abdomen of a mouse at 13 days of pregnancy is swabbed with 70% ethanol, and the decidua is removed into phosphate buffered saline (PBS). Embryos are harvested; placenta, membranes, and soft tissues are removed; and the carcasses are washed twice in PBS. They are then transferred to fresh 10 cm bacterial dishes containing 2 mL trypsin/EDTA, and finely minced. After incubating 5 min at 37° C., the trypsin is inactivated with 5 mL DMEM containing 10% FBS, and the mixture is transferred to a 15 mL conical tube. Debris is allowed to settle for 2 min, the supernatant is made up to a final volume of 10 mL, and plated onto a 10 cm tissue culture plate or T75 flask. The flask is incubated undisturbed for 24 h, after which the medium is replaced. When flasks are confluent (~2-3 d), they are split 1:2 into new flasks.

Feeder cells are propagated in mEF medium, containing 90% DMEM (Gibco #11965-092), 10% FBS (Hyclone #30071-03), and 2 mM glutamine. mEFs are propagated in T150 flasks (Corning #430825), splitting the cells 1:2 every other day with trypsin, keeping the cells subconfluent. To prepare the feeder cell layer, cells are irradiated at a dose to inhibit proliferation but permit synthesis of important factors that support hES cells (~4000 rads gamma irradiation). Six-well culture plates (such as Falcon #304) are coated by incubation at 37° C. with 1 mL 0.5% gelatin per well overnight, and plated with 375,000 irradiated mEFs per well. Feeder cell layers are used 5 h to 4 days after plating. The medium is replaced with fresh hES medium just before seeding.

hES cells can be isolated from human blastocyst obtained from human in vivo preimplantation embryos, in vitro fertilized embryos, or one cell human embryos expanded to the blastocyst stage (Bongso et al., Hum Reprod 4: 706, 1989). Human embryos can be cultured to the blastocyst stage in G1.2 and G2.2 medium (Gardner et al., Fertil. Steril. 69:84, 1998). The zona pellucida is removed from blastocysts by brief exposure to pronase (Sigma). The inner cell masses are isolated by immunosurgery or by mechanical separation, and plated on mouse embryonic feeder layers, or in feeder free culture as described below.

After 9 to 15 days, inner cell mass-derived outgrowths are dissociated into clumps either by exposure to calcium and magnesium-free phosphate-buffered saline (PBS) with 1 mM EDTA, by exposure to dispase, collagenase or trypsin, or by mechanical dissociation with a micropipette; and then replated on mEF in fresh medium. Dissociated cells are replated on mEF feeder layers in fresh ES medium, and observed for colony formation. Colonies demonstrating undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1-2 weeks by brief trypsinization, exposure to Dulbecco's PBS (without calcium or magnesium and with 2 mM EDTA), exposure to type IV collagenase (~200 U/mL; Gibco) or by selection of individual colonies by micropipette.

Propagation of pPS Cells in the Absence of Feeder Cells

This invention allows pPS to be propagated in an undifferentiated state, even in the absence of feeder cells. Feeder-free pPS cell cultures can be obtained either by passaging cells grown on feeder into feeder-free conditions, or by first deriving the cells from blastocysts into a feeder-free environment.

In the absence of feeders, the pPS cells are cultured in an environment that supports proliferation without differentiation. Aspects of culture that can affect differentiation include the substrate upon which the cells are cultured, the medium in which they are cultured, and the manner in which they are split and passaged to new culture environments.

pPS cells may be supported in feeder-free culture on an extracellular matrix. The matrix can be deposited by preculturing and lysing a matrix-forming cell line (WO 99/20741), such as the STO mouse fibroblast line (ATCC Accession No. CRL-1503), or human placental fibroblasts. The matrix can also be coated directly into the culture vessel with isolated matrix components. Matrigel® is a soluble preparation from Engelbreth-Holm-Swarm tumor cells that gels at room temperature to form a reconstituted basement membrane. Other suitable extracellular matrix components may include laminin, fibronectin, proteoglycan, entactin, heparan sulfate, and so on, alone or in various combinations. Substrates that can be tested using the experimental procedures described herein include not only other extracellular matrix components, but also polyamines, and other commercially available coatings. This invention contemplates adding extracellular matrix to the fluid phase of a culture at the time of passaging the cells or as part of a regular feeding. This invention also contemplates extracellular matrix deposited into the culture by cells within the culture (such as pPS cells that have formed around the periphery of an undifferentiated colony).

The pluripotent cells are plated onto the substrate in a suitable distribution and in the presence of a medium that promotes cell survival, propagation, and retention of the desirable characteristics. These characteristics benefit from careful attention to the seeding distribution. One feature of the distribution is the plating density. It has been found that plating densities of at least ~15,000 cells $cm^{-2}$ (typically 90,000 $cm^{-2}$ to 170,000 $cm^{-2}$) promote survival and limit differentiation.

Another consideration is cell dispersion. In one method, enzymatic digestion is halted before cells become completely dispersed (say, ~5 min with collagenase IV). The plate is then scraped gently with a pipette, and the cells are triturated into clumps of adherent cells, about 10-2000 cells in size, which are then passaged into the new culture environment. Alternatively, primate PS cells can be passaged between feeder-free cultures as a finer cell suspension, providing that an appropriate enzyme and medium are chosen, and the plating density is sufficiently high. By way of illustration, confluent human embryonic stem cells cultured in the absence of feeders are removed from the plates by incubating with 0.05% (wt/vol) trypsin and 0.053 mM EDTA for 5-15 min at 37° C. The remaining cells in the plate are removed, triturated with the pipette until dispersed into single cells and small clusters, and then replated. In another illustration, the cells are harvested without enzymes before the plate reaches confluence. The cells are incubated ~5 min in 0.5 mM EDTA alone in PBS, washed from the culture vessel, and then replated without further dispersal.

pPS cells plated in the absence of fresh feeder cells benefit from being cultured in a nutrient medium. The medium will generally contain the usual components to enhance cell survival, including isotonic buffer, essential minerals, and either serum or a serum replacement of some kind. To inhibit differentiation, the medium is formulated to supply some of the elements provided by feeder cells or their equivalents.

The base nutrient medium used for conditioning can have any of several different formulae. Exemplary serum-containing ES medium is made with 80% DMEM (typically KO DMEM), 20% defined fetal bovine serum (FBS), 1% non-essential amino acids, 1 mM L-glutamine, and 0.1 mM β-mercaptoethanol. Serum-free ES medium is made with 80% KO DMEM, 20% serum replacement, 1% non-essential amino acids, 1 mM L-glutamine, and 0.1 mM β-mercaptoethanol. Not all serum replacements work; an effective serum replacement is Gibco #10828-028.

Other suitable base media are X-VIVO™ 10 expansion medium (Biowhittaker) and QBSF™-60 (Quality Biological Inc.) (Example 8). See also WO 98/30679 (Life Technologies Inc.) and U.S. Pat. No. 5,405,772 (Amgen). The medium will typically contain a protein nutrient, in the form of serum (such as FBS), serum replacement, albumin, or essential and non-essential amino acids in an effective combination. It will also typically contain lipids, fatty acids, or cholesterol as artificial additives or the HDL or LDL extract of serum. Other beneficial factors that can be included are hormones like insulin or transferrin, nucleosides or nucleotides, pyruvate, and a reducing agent such as β-mercaptoethanol.

Medium Additives

The nutrient medium used for culturing the pPS cells comprises one or more factors that promote proliferation of the pPS cells without differentiation. As will be apparent from the following description, the supplementation can occur by pre-culturing the medium with cells that secrete such factors, by adding such factors to the medium artificially, or by both techniques in combination.

Conditioned medium can be prepared by culturing irradiated primary mouse embryonic fibroblasts (Example 1) or other cells (Example 4) at a density of ~5-6×10$^4$ cm$^{-2}$ in a serum free medium such as KO DMEM supplemented with 20% serum replacement and ~4-8 ng/mL basic fibroblast growth factor (bFGF). The culture supernatant is harvested after ~1 day at 37° C. The cells are cultured in the medium for sufficient time to allow adequate concentration of released factors that support pPS cell culture. Typically, medium conditioned by culturing for 24 hours at 37° C. contains a concentration of factors that support pPS cell culture for at least 24 hours. However, the culturing period can be adjusted upwards or downwards, determining empirically what constitutes an adequate period. Medium that has been conditioned for 1-2 days is typically used to support pPS cell culture for 1-2 days, and then exchanged.

Non-conditioned medium that supports pPS cell growth in an undifferentiated state can be created by adding to a suitable base medium certain factors that invoke the appropriate signal transduction pathways in undifferentiated cells.

It has been discovered that the fibroblast growth factor family is especially effective in this regard. Exemplary are basic FGF (FGF-2), and FGF-4, but other members of the family can also be used. Also suitable are species homologs, artificial analogs, antibodies to the respective FGF receptor, and other receptor activator molecules. It has been determined from gene expression analysis that undifferentiated hES cells express receptors for acidic FGF (FGF-1). At a sufficient concentration (40 ng/mL, depending on other conditions), FGF alone is sufficient to promote growth of hES cells in an undifferentiated state (Examples 6 and 8).

This invention includes a method for determining additional factors that facilitate the action of FGF and equivalents in their support of undifferentiated pPS cell growth. The method involves combining a plurality of factors into functional groups, and culturing the cells with the groups in various combinations. Once the effective groups are determined, the rest can be eliminated, and the group can be dissected to determine the minimal effective combination. This strategy is illustrated in Example 7.

As a supplement to FGF, ligands that bind c-kit, such as stem cell factor (SCF, Steel factor), antibodies to c-kit, and other activators of the same signal transduction pathway may also be beneficial. SCF is dimeric and occurs in soluble and membrane-bound forms. It transduces signals by ligand-mediated dimerization of c-kit, which is a receptor tyrosine kinase related to the receptors for platelet-derived growth factor (PDGF), macrophage colony-stimulating factor, Flt-3 ligand and vascular endothelial growth factor (VEGF). Also of interest are factors that elevate cyclic AMP levels, such as forskolin. These factors or their equivalents may be used individually or in an effective combination with other influential factors in the medium, as already described.

The formulations provided in the Example section below were primarily designed for culturing hES cells. Where appropriate, the illustrations in this disclosure can be adapted to other types of pPS cells and multipotent cells by accommodating the known properties of the cells. For example, the hEG cells claimed in U.S. Pat. No. 6,090,622 are dependent on the presence of both bFGF and an inducer of gp130 (such as LIF or Oncostatin-M). The culture media for growing hEG cells can be adapted accordingly.

Each of the conditions described here can be optimized independently, and certain combinations of conditions will prove effective upon further testing. Such optimization is a matter of routine experimentation, and does not depart from the spirit of the invention provided in this disclosure.

Desirable Outcomes

A medium formulation can be tested for its ability to support pPS cells by swapping it into a feeder-free culture system in place of medium conditioned by primary mouse embryonic fibroblasts (mEF), or some other proven standard (Examples 5-8). If pPS cells grow in a substantially undifferentiated state, then the medium can be characterized as supporting pPS cells in feeder free culture.

One of the virtues of using fresh medium in this culture system is the ability to adjust conditions so that the cells expand more rapidly than they do when cultured on feeder cells according to traditional techniques, or in conditioned medium. Populations of pluripotent stem cells can be obtained that are 10-, 20-, 50-, 100-, or 1000-fold expanded when compared to the starting population. Under suitable conditions, cells in the expanded population will be 50%, 70% or more in the undifferentiated state.

The degree of expansion per passage is calculated by dividing the number of cells harvested at the end of the culture by the number of cells originally seeded into the culture. Where geometry of the culture environment is limiting or for other reasons, the cells may optionally be passaged into a similar culture environment for further expansion. The total expansion is the product of all the expansions in each of the passages. Of course, it is not necessary to retain all the expanded cells on each passage. For example, if the cells expand 2-fold in each culture, but only ~50% of the cells are retained on each passage, then approximately the same number of cells will be carried forward. But after 4 cultures, the cells are said to have undergone an expansion of 16-fold.

Cultures of hES cells on mouse embryonic fibroblast (mEF) feeder cells, or in mEF conditioned medium, have a doubling time of about 31-33 hours (Example 1). Certain culture environments of this invention comprising fresh medium support doubling of hES cells in less than ~24 hours (Example 8), potentially in less than ~16 hours. In terms of expansion upon regular passaging in standard culture wells, the system can be used to expand hES cells by 10- to potentially 50-fold per week. Improved efficiency is believed to be the result both of the more rapid doubling time, and the higher proportion of pPS cells that take in the new environment after passaging.

Of course, culture conditions inappropriate for pPS cells will cause them to differentiate promptly. However, the reader should be aware that marginally beneficial conditions may allow pPS cells to go through a few passages while still retaining a proportion of undifferentiated cells. In order to test whether conditions are adequate for indefinite culture of pPS cells, it is recommended that the cells be expanded at least 10- or 20-fold though at least 4 passages. A higher degree of expansion and/or a higher number of passages (e.g., at least 7 passages and 50- or 100-fold expansion) provides a more rigorous test. It is permissible for a few phenotypic markers to undertake a quantitative adjustment befitting adaptation to particular conditions (say, up or down 2- or 5-fold)—they will typically revert to previous levels when the cells are placed back into their previous environment (Example 8). An effective test for whether a cell is still pluripotent is the demonstration that the cell can still be caused to differentiate into progeny that represents (or bears antibody or PCR-detectable phenotypes) of each of the three embryonic germ layers.

Nutrient medium and other culture characteristics formulated according to this invention can be adapted to any culture device suitable for growing pPS cells. Devices having a suitable surface include regular tissue culture wells, T-flasks, roller bottles, gas-permeable containers, and flat or parallel plate bioreactors. Also contemplated are culture environments in which the pPS cells are attached to microcarriers or particles kept in suspension in stirred tank vessels. Fresh medium can be introduced into any of these environments by batch exchange (replacement of spent medium with fresh medium), fed-batch process (fresh medium added with no removal), or ongoing exchange in which a proportion of the medium is replaced with fresh medium on a continuous or periodic basis.

Characteristics of Undifferentiated pPS Cells

Human ES cells have the characteristic morphological features of undifferentiated stem cells. In the two dimensions of a standard microscopic image, hES cells have high nuclear/cytoplasmic ratios in the plane of the image, prominent nucleoli, and compact colony formation with poorly discernable cell junctions. Cell lines can be karyotyped using a standard G-banding technique (available at many clinical diagnostics labs that provides routine karyotyping services, such as the Cytogenetics Lab at Oakland Calif.) and compared to published human karyotypes. It is desirable to obtain cells that have a "normal karyotype", which means that the cells are euploid, wherein all human chromosomes are present and are not noticeably altered.

hES and hEG cells can also be characterized by expressed cell markers detectable by antibody (flow cytometry or immunocytochemistry) or by reverse transcriptase PCR. Human ES cells typically have antibody-detectable SSEA-4, Tra-1-60, and Tra-1-81, but little SSEA-1. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.). Expression of hTERT and OCT-4 (detectable by RT-PCR) and telomerase activity (detectable by TRAP assay) are also characteristic of many types of undifferentiated pPS cells (Example 3).

Another desirable feature of propagated pPS cells is a potential to differentiate into cells of all three germ layers: endoderm, mesoderm, and ectoderm. Pluripotency of hES cells can be confirmed by forming teratomas in SCID mice, and examining them for representative tissues of all three germ layers. Alternatively, pluripotency can be determined by allowing pPS cells to differentiate non-specifically (for example, by forming embryoid bodies), and then determining the cell types represented in the culture by immunocytochemistry (FIG. 10). Potential of pPS cells to differentiate into particular cell lines can be determined according to procedures described later in this disclosure.

Certain cell populations described in this disclosure are substantially undifferentiated, and can be passaged between multiple cultures in the conditions described. During passage, some cells may differentiate (particularly when replated as single cells at low density, or when large clusters are allowed to form). However, cultures typically reestablish a larger proportion of undifferentiated cells as they reapproach confluence.

Genetic Alteration of Pluripotent Stem Cells

This disclosure also provides a system for obtaining pPS cells that have been genetically altered, either in a transient or stable fashion. The cells may be modified to give them desired properties in the undifferentiated state, to give them desired properties after differentiation into other cell types, or to provide a method to positively or negatively select for particular undifferentiated or differentiated phenotypes.

For therapeutic applications, it may be beneficial to modify cells with therapeutic genes, or to render cells histocompatible with the intended recipient. Genetic alteration can also be used to prepare cells for sorting after differentiation. For example, the hES cells are transfected with a drug susceptibility gene, such as herpes simplex virus thymidine kinase (which renders cells susceptible to ganciclovir), under control of a promoter specific for undifferentiated cells, such as the OCT-4 promoter or the hTERT promoter (WO 02/42445). After the culture has been made to differentiate, residual undifferentiated cells can be eliminated from the population using ganciclovir.

Suitable vector plasmids for transfecting into hES cells include lipid/DNA complexes, such as those described in U.S. Pat. Nos. 5,578,475; 6,020,202; and 6,051,429. Suitable reagents for making DNA-lipid complexes include lipofectamine (Gibco/Life Technologies #11668019) and FuGENE™ 6 (Roche Diagnostics Corp. #1814443); and LipoTAXI™ (Invitrogen Corp., #204110). Viral vector systems for producing hES cells with stable genetic alterations can be based on adenovirus, retrovirus, or lentivirus, prepared using commercially available virus components.

Genetic alteration of hES cells requires achieving sufficiently high efficiency of genetic alteration, while not promoting differentiation of the hES cells along an undesired pathway.

Efficiencies of genetic alteration are rarely 100%, and it is usually desirable to enrich the population for cells that have been successfully altered. The genetically altered cells can be enriched by taking advantage of a functional feature of the new genotype. For example, where the pPS cells are transfected with a label such as GFP, or with an immunostainable surface marker such as NCAM, then the pPS cells can be suspended, separated by fluorescence-activated cell sorting, and replated. The reader is cautioned that complete dissociation of pPS cells usually promotes differentiation.

A particularly effective way of enriching genetically altered cells is positive selection using resistance to a drug such as neomycin. To accomplish this, the cells can be genetically altered by contacting simultaneously with vector systems for the marker gene or gene of interest, and a vector system that provides the drug resistance gene. If the proportion of drug resistance gene in the mixture is low (say, 3:1), then most drug resistant cells should also contain the gene of interest. Alternatively, the drug resistance gene can be built into the same vector as the gene of interest. After transfection has taken place, the cultures are treated with the corresponding drug, and untransfected cells are eliminated.

pPS cells are especially amenable to genetic alteration when they are grown in feeder-free culture, elaborated throughout this disclosure. Transient transfection using DNA/lipid complexes can be as high as 60%. The cells are easier to manipulate, and there are no feeder cells around to act as a sink for the vector. Drug selection does not require availability of a drug-resistant feeder cell. The number of undifferentiated pPS colonies that grow out after transfection may also be improved.

Following genetic alteration and drug selection (on drug-resistant feeders or feeder-free culture), it is possible to pick colonies that demonstrate the altered phenotype, and culture them separately. The picked colonies are dispersed into small clumps of 25-100 cells, and replated in a suitable environment. It is possible to achieve cultures of pPS cells in which a high proportion (up to 90%) of the undifferentiated cells are genetically altered.

Differentiation of Propagated pPS Cells pPS cells cultured according to this invention can be used to make differentiated cells of various commercially and therapeutically important tissue types.

For example, scientists at Geron Corporation have discovered methods for obtaining highly enriched populations of cells of the neural lineage. Cells are changed to a culture medium containing one or more neurotrophins (such as neurotrophin 3 or brain-derived neurotrophic factor) and one or more mitogens (such as epidermal growth factor, basic fibroblast growth factor, platelet-derived growth factor, insulin-like growth factor 1, and erythropoietin). Cultured cells are optionally separated based on whether they express a marker such as A2B5 or NCAM. Neural precursors can be obtained having the capacity to generate both neuronal cells (including mature neurons), and glial cells (including astrocytes and oligodendrocytes). Alternatively, replicative neuronal precursors can be obtained that have the capacity to form differentiated cell populations in which at least ~5% of all the cells in the population express tyrosine hydroxylase, a marker of dopaminergic neurons. See PCT publication WO 01/88104 and PCT application PCT/US01/15861.

Scientists at Geron Corporation have discovered that culturing pPS cells or embryoid body cells in the presence of a histone deacetylase inhibitor such as n-butyrate creates a population of cells highly enriched for markers of the hepatocyte lineage. The cultured cells are optionally cultured simultaneously or sequentially with a hepatocyte maturation factor, such as EGF, insulin, and FGF. Further details can be found in PCT publication WO 01/81549.

Scientists at Geron Corporation have developed methods for generating and purifying hES cell derived cells that have characteristic markers of cardiomyocytes and spontaneous periodic contractile activity. Differentiation is facilitated by nucleotide analogs that affect DNA methylation (such as 5-aza-deoxy-cytidine), growth factors, and bone morphogenic proteins. The cells can be further enriched by density-based cell separation, and maintained in media containing creatine, carnitine, and taurine. See PCT application PCT/US02/22245.

Scientists at Geron Corporation have also discovered methods for differentiating hES cells into mesenchymal cells in a medium containing a bone morphogenic protein (BMP), a ligand for the human TGF-β receptor, or a ligand for the human vitamin D receptor. The medium may further comprise dexamethasone, ascorbic acid-2-phosphate, and sources of calcium and phosphate. Under certain circumstances, derivative cells can have phenotypic features of cells of the osteoblast lineage. See PCT application PCT/US02/20998.

For therapeutic use, it is usually desirable that differentiated cell populations be substantially free of undifferentiated pPS cells. One way of depleting undifferentiated stem cells from the population is to transfect them with a vector in which an effector gene under control of a promoter (such s the TERT promoter) that causes preferential expression in undifferentiated cells. For further elaboration, the reader is referred to PCT publication WO 02/42445.

Uses of Propagated pPS Cells and their Derivatives

This description provides a method by which large numbers of pluripotent cells can be produced commercially without the need of feeder cells, and then differentiated into committed precursor cells or terminally differentiated cells. These cell populations can be used for a number of important purposes. The use of pPS cells for genomic analysis or to produce transcript libraries and specific antibodies is further detailed in PCT publication WO 01/51616.

Screening Proliferation Factors, Differentiation Factors, and Pharmaceuticals pPS cells can be used to screen for factors (such as small molecule drugs, peptides, polynucleotides, and the like) or conditions (such as culture conditions or manipulation) that affect the characteristics of pPS cells in culture. This system has the advantage of not being complicated by a secondary effect caused by perturbation of the feeder cells by the test compound. In one application, growth affecting substances are tested. The conditioned medium is withdrawn from the culture and a simpler medium (such as KO DMEM) is substituted. Different wells are then treated with different cocktails of soluble factors that are candidates for replacing the components of the conditioned medium. Efficacy of each mixture is determined if the treated cells are maintained and proliferate in a satisfactory manner, optimally as well as in conditioned medium. Potential differentiation factors or conditions can be tested by treating the cells according to the test protocol, and then determining whether the treated cell develops functional or phenotypic characteristics of a differentiated cell of a particular lineage.

Feeder-free pPS cultures can also be used for the testing of pharmaceutical compounds in drug research. Assessment of the activity of candidate pharmaceutical compounds generally involves combining the differentiated cells of this invention with the candidate compound, determining any resulting change, and then correlating the effect of the compound with the observed change. The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity (Castell et al., pp 375-410 in *In vitro Methods in Pharmaceutical Research*, Academic Press, 1997). Cytotoxicity can be determined by the effect on cell viability, survival, morphology, on the expression or release of certain markers, receptors or enzymes, on DNA synthesis or repair, measured by [$^3$H]-thymidine or BrdU incorporation, or on sister chromatid exchange, determined by metaphase spread. The reader is referred generally to the standard textbook *In vitro Methods in Pharmaceutical Research*, Academic Press, 1997, and U.S. Pat. No. 5,030,015.

Therapeutic Compositions

Differentiated cells of this invention can also be used for tissue reconstitution or regeneration in a human patient in need thereof. The cells are administered in a manner that permits them to graft to the intended tissue site and reconstitute or regenerate the functionally deficient area.

In one example, neural stem cells are transplanted directly into parenchymal or intrathecal sites of the central nervous system, according to the disease being treated. Grafts are done using single cell suspension or small aggregates at a density of 25,000-500,000 cells per µL (U.S. Pat. No. 5,968, 829). The efficacy of neural cell transplants can be assessed in a rat model for acutely injured spinal cord as described by McDonald et al. (Nat. Med. 5:1410, 1999), and Kim et al. (Nature 418:50, 2002). A successful transplant will show transplant-derived cells present in the lesion 2-5 weeks later, differentiated into astrocytes, oligodendrocytes, and/or neurons, and migrating along the cord from the lesioned end, and an improvement in gait, coordination, and weight-bearing.

The efficacy of cardiomyocytes can be assessed in an animal model for cardiac cryoinjury, which causes 55% of the left ventricular wall tissue to become scar tissue without treatment (Li et al., Ann. Thorac. Surg. 62:654, 1996; Sakai et al., Ann. Thorac. Surg. 8:2074, 1999, Sakai et al., J. Thorac. Cardiovasc. Surg. 118:715, 1999). Successful treatment will reduce the area of the scar, limit scar expansion, and improve heart function as determined by systolic, diastolic, and developed pressure. Cardiac injury can also be modeled using an embolization coil in the distal portion of the left anterior descending artery (Watanabe et al., Cell Transplant. 7:239, 1998), or by ligation of the left anterior descending coronary artery (Min et al., J. Appl. Physiol. 92:288, 2002). Efficacy of treatment can be evaluated by histology and cardiac function. Cardiomyocyte preparations embodied in this invention can be used in therapy to regenerate cardiac muscle and treat insufficient cardiac function (U.S. Pat. No. 5,919,449 and WO 99/03973).

Hepatocytes and hepatocyte precursors can be assessed in animal models for ability to repair liver damage. One such example is damage caused by intraperitoneal injection of D-galactosamine (Dabeva et al., Am. J. Pathol. 143:1606, 1993). Efficacy of treatment can be determined by immunocytochemical staining for liver cell markers, microscopic determination of whether canalicular structures form in growing tissue, and the ability of the treatment to restore synthesis of liver-specific proteins. Liver cells can be used in therapy by direct administration, or as part of a bioassist device that provides temporary liver function while the subject's liver tissue regenerates itself following fulminant hepatic failure.

For purposes of commercial distribution, cells prepared according to this invention are typically supplied in the form of a pharmaceutical composition comprising an isotonic excipient, and prepared under conditions that are sufficiently sterile for human administration. For general principles in medicinal formulation of cell compositions, the reader is referred to *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000. The cells may be packaged in a device or container suitable for distribution or clinical use, optionally accompanied by information relating to use of the cells in tissue regeneration, or restoring a therapeutically important metabolic function.

The examples that follow are provided by way of further illustration, and are not meant to imply any limitation in the practice of the claimed invention.

EXAMPLES

Example 1

Growing hES Cells without Feeder Cells in Conditioned Medium

In this example, undifferentiated hES cells that had been maintained on primary mouse embryonic feeder cells were maintained in the absence of feeders. The culture wells were coated with Matrigel®, and the cells were cultured in the presence of conditioned nutrient medium obtained from a culture of irradiated primary fibroblasts.

Conditioned medium (CM) was prepared as follows. The fibroblasts were harvested from T150 flasks by washing once with $Ca^{++}/Mg^{++}$ free PBS and incubating in trypsin/EDTA (Gibco). After the fibroblasts detached from the flask, they were collected in mEF medium (DMEM+10% FBS). The cells were irradiated at 4000 rad, counted and seeded at about 55,000 cells $cm^{-2}$ in mEF medium. After at least 4 hours, the medium was exchanged with SR containing ES medium. Conditioned medium was collected daily for feeding of hES cultures. Alternatively, medium was prepared using mEF plated in culture flasks, exchanging medium daily at 0.3-0.4 mL $cm^{-2}$. Before addition to the hES cultures, the conditioned medium was supplemented with 4 ng/mL of human bFGF (Gibco). Fibroblast cultures were used in this system for about 1 week, before replacing with newly prepared cells.

Undifferentiated hES colonies were harvested from hES cultures on feeders as follows. Cultures were incubated in ~200 U/mL collagenase IV for about 5 minutes at 37° C. Colonies were harvested by picking individual colonies up with a 20 µL pipet tip under a microscope or by scraping and dissociating into small clusters in conditioned medium (CM). These cells were then seeded onto Matrigel® coated plates (0.75-1 mL diluted ~1:30) in conditioned medium at 15 colonies to each 9.6 $cm^2$ well.

The day after seeding on Matrigel®, hES cells were visible as small colonies and there were cells in between the colonies that appeared to be differentiating or dying. As the hES cells proliferated, the colonies became quite large and very compact, representing the majority of surface area of the culture dish. The hES cells in the colonies had a high nucleus to cytoplasm ratio and had prominent nucleoli, similar to hES cells maintained on feeder cells. At confluence, the differentiated cells in between the colonies represented less than 10% of the cells in the culture.

Six days after seeding, the cultures had become almost confluent. The cultures were split using Collagenase IV, gently triturated into small clusters of 10-2,000 cells, and then re-seeded on Matrigel® coated plates in conditioned medium at ~90,000 to 170,000 cells $cm^{-2}$. Medium was changed daily, and the cells were split and passaged again at 13 and 19 days after initial seeding.

Cultures of hES cells have been grown in the absence of feeder cells for over 147 days after initial seeding, with no apparent change in the proliferative capacity or phenotype. Human ES cells maintained on Matrigel® in mEF conditioned medium have a doubling time of about 31-33 hours, similar to the proliferation rate for hES cells grown on mEF feeder cells. H1 cells after 64 days of feeder-free culture showed a normal karyotype.

hES cells seeded onto laminin, fibronectin or collagen IV had colonies of undifferentiated hES cells, although the cultures on fibronectin or collagen IV did not contain as many undifferentiated colonies as the cultures on Matrigel® or laminin. When cells on Matrigel® or laminin reached confluence, the cells within the colonies became very compact, were morphologically very similar to the cells maintained on feeders and were serially passaged. After 40 days (6 passages), cells on Matrigel® and laminin contained a high proportion of colonies which continued to display ES-like morphology in long term culture. However, cells maintained on fibronectin or collagen IV had fewer colonies displaying appropriate ES-morphology. As controls, cells cultured on Matrigel® or laminin in non-conditioned medium appeared to be proliferating more slowly and showed a differentiated morphology after a few passages.

FIG. 1 shows the morphology of hES cells in feeder-free culture. Panel A (Left Side) shows morphology of hES cells of the H1 line cultured on feeder cells in non-conditioned medium (mEF/RM), on Matrigel®, laminin, fibronectin, or collagen IV in mEF conditioned medium. Panel B shows morphology of hES cells of the H9 line maintained on Matrigel® in various types of conditioned medium, described in Example 4.

Human ES cells maintained on Matrigel® in mEF conditioned medium showed a doubling time of about 31-33 hours, similar to the proliferation rate for hES cells grown on mEF feeder cells. H1 cells after 64 days of feeder-free culture showed a normal karyotype.

Example 2

Phenotypic Markers of hES Cells in Feeder-Free Culture

Undifferentiated hES cells express SSEA-4, Tra-1-60, Tra-1-81, OCT-4, and hTERT. In order to assess whether the cells maintained in feeder-free conditions retained these markers, cells were evaluated by immunostaining, reverse transcriptase PCR amplification, and assay for telomerase activity.

For analysis by fluorescence-activated cell sorting (FACS), the hES cells were dissociated in 0.5 mM EDTA in PBS and resuspended to about $5 \times 10^5$ cells in 50 μL diluent containing 0.1% BSA in PBS. They were labeled with specific primary antibody and then fluorescent second antibody, and analyzed on a Flow Cytometer.

Similar to the hES cells on feeders, cells on Matrigel®, laminin, fibronectin or collagen IV expressed SSEA-4, Tra-1-60 and Tra-1-81. There was very little expression of SSEA-1, a glycolipid that is not expressed by undifferentiated hES cells.

FIG. 2 shows marker expression detected by immunocytochemistry. Cells were incubated with primary antibody, fixed in 2% paraformaldehyde, and then visualized with FITC-conjugated goat anti-mouse immunoglobulin. The results show that SSEA-4, Tra-1-60, Tra-1-81, and alkaline phosphatase were expressed by the hES colonies on Matrigel® or laminin, as seen for the cells on feeders—but not by the differentiated cells in between the colonies.

Quantitative data on day 19 after initial seeding is shown in the following table.

TABLE 1

Phenotype of hES Cells Grown in the Absence of Feeder Cells

| Marker | Specificity | Percentage of Cells Staining |
|---|---|---|
| SSEA-4 | undifferentiated cells | 92% |
| Tra-1-60 | undifferentiated cells | 92% |

TABLE 1-continued

Phenotype of hES Cells Grown in the Absence of Feeder Cells

| Marker | Specificity | Percentage of Cells Staining |
|---|---|---|
| Tra-1-81 | undifferentiated cells | 83% |
| SSEA-1 | differentiated cells | 12% |

FIG. 3 shows OCT-4 and hTERT expression of H1 cells grown on feeders or in a feeder free environment, as detected by reverse-transcriptase PCR amplification (detailed in WO 01/51616).

The POU transcription factor OCT-4 is normally expressed in the undifferentiated hES cells and is down-regulated upon differentiation. In this experiment, it was found that the cells maintained on Matrigel® or laminin in conditioned medium (CM) for 21 days express OCT-4, whereas cells maintained in Matrigel® in unconditioned regular medium (RM) did not. Cells maintained on fibronectin or collagen IV, which showed a large degree of differentiation, expressed lower levels of OCT-4 compared to cells on feeders, Matrigel® or laminin. hTERT and OCT-4 expression was seen in all the culture conditions except Matrigel® and regular medium. After exposure of cells to retinoic acid (RA) or dimethyl sulfoxide (DMSO), factors that promote cell differentiation, the expression of hTERT was markedly decreased.

Telomerase activity was measured by telomeric repeat amplification protocol (TRAP assay: Kim et al., Science 266: 2011, 1997; Weinrich et al., Nature Genetics 17:498, 1997). All the cultures conditions showed positive telomerase activity after 40 days on Matrigel®, laminin, fibronectin or collagen IV in mEF conditioned medium.

Example 3

Pluripotency of hES Cells in Feeder-Free Culture

In vitro differentiation was induced in H1 hES cells maintained in conditioned medium on Matrigel®, laminin, fibronectin or collagen IV for 26 days. The hES cells were dissociated into small clumps by incubating in ~200 U/mL collagenase IV at 37° C. for 10 min, and cultured in suspension to form embryoid bodies (EBs) in medium containing DMEM, 20% FBS (Hyclone), 1 mM glutamine, 0.1 mM β-mercaptoethanol, and 1% non-essential amino acids (Gibco). After 4 days in suspension, the aggregates were transferred onto poly-ornithine-coated plates, and cultured for additional 7 days. The cultures were then examined for the presence of beating cells, and processed for immunocytochemistry.

The staining patterns were consistent with cells of the neuron and cardiomyocyte lineages (β-tubulin III and cardiac troponin I, respectively). About 8 days after differentiation, beating regions were identified in all cultures. There were also cells staining for α-fetoprotein, a marker of endoderm lineage.

hES cells were also tested for their ability to form teratomas by intramuscular injection into SCID mice. Cells maintained on feeders or off feeders were harvested, resuspended in PBS and injected intramuscularly into SCID/beige mice ($5 \times 10^6$ cells per site). Tumors were excised and processed for histological analysis. Cystic epithelial structures, probable dental component, cartilage and glandular epithelial or neural components were found in teratomas derived from feeder-free hES cultures.

Example 4

Sources of Conditioned Medium for Feeder-Free Culture

Media conditioned by several cell lines were tested for their ability to support the growth of hES cells in feeder-free culture. Isolation of primary mouse embryonic fibroblasts (mEF) is described above. The NHG190 cell line is a telomerized mouse embryonic fibroblast line described in WO 01/51616. STO is a transformed mouse fibroblast line available from the ATCC. BJ 5ta is a telomerized human foreskin fibroblast cell line. hTERT-RPE is a telomerized human retinal epithelial cell line.

To prepare conditioned medium, the respective cell lines were harvested by washing once with $Ca^{++}/Mg^{++}$ free PBS, incubating in trypsin/EDTA (Gibco) for about 5 min, and suspending in mEF medium. The cells were irradiated at ~4000 rad, counted, and plated into culture vessels. After at least 4 h, the medium was exchanged with ES medium containing 4 ng/mL bFGF. Conditioned medium was collected daily thereafter, and used for feeding of hES cultures. Before addition to the hES cultures, each conditioned medium was supplemented with 4 ng/mL of human basic fibroblast growth factor (hbFGF; Gibco).

FIG. 1, Panel B (Right Side) shows morphology of hES cells of the H9 line maintained on Matrigel® in medium conditioned by mEF, NHG190, STO and BJ 5ta cells, compared with unconditioned regular medium (RM). The cells in RPE conditioned medium differentiated within the first week of culture. The cells in the other conditioned mediums all had hES colonies with appropriate ES-morphology. Based on the morphology, confluence of the culture, and the ratio of differentiated to undifferentiated cells the conditioned medium can be ranked in order of decreasing preference: primary mEF, NHG190, STO, and BJ 5ta.

Similar to cells maintained in conditioned medium from primary mEF, cells on Matrigel® or laminin in medium conditioned by other cell lines, including NHG190, STO and BJ 5ta, expressed high levels of SSEA-4, Tra-1-60 and Tra-1-81 but low levels of SSEA-1 as analyzed by FACS analysis. Cells on Matrigel® or laminin in mEF conditioned medium or NHG190 conditioned medium were able to differentiate into three germ layer cell types. Immunocytochemical analysis of the differentiated cultures showed positive staining for β-tubulin III consistent with neurons (ectoderm lineage), cardiac troponin I consistent with cardiomyocytes (mesoderm lineage), and α-fetoprotein, consistent with cells of the endoderm lineage.

To determine if leukemia inhibitory factor (LIF) can substitute for conditioned medium in maintaining hES cells without feeders, cells of the H1 and H9 line were cultured on Matrigel® in ES medium containing LIF at a final concentration of 1500, 1,000, or 500 U/mL (recombinant LIF from R&D systems; Catalog #250-L). Cells were simultaneously cultured in mEF conditioned medium as the positive control, and unconditioned ES medium as negative control. After one week, cultures in medium either with or without LIF showed a large degree of differentiation, while cultures maintained in mEF conditioned medium contained predominately undifferentiated colonies. These data indicate that LIF alone will not maintain hES cells in an undifferentiated state at the concentrations tested, in the absence of feeder cells.

Example 5

Genetic Alteration of hES Cells in Feeder-Free Culture hES cells maintained in feeder-free culture on laminin in conditioned medium were genetically modified by transfecting with a plasmid carrying green fluorescent protein (GFP) driven by the CMV promoter.

hES cells of the H9 line maintained on laminin in mEF-conditioned medium were transfected with a plasmid carrying GFP driven by the CMV promoter (ClonTech cat. #6084-1) at 24 or 48 h after plating. Initial experiments used a mixture of 5 μg of plasmid and 12 μL of Lipofectamine 2000™ (Gibco, cat #11668-019). Cells received 1 mL of DNA/lipid complex and were incubated for 4 h at 37° before the addition of 3 mL of mEF-conditioned medium, and then monitored for GFP expression 24 h after transfection.

FIG. 4 shows the results of this experiment. Panel A: morphology of H9 cells maintained on laminin. Panel B: GFP-positive cells observed in the same colony shown in A. Panel C: FACS analysis of % GFP-positive cells in SSEA-4 high population (undifferentiated cells). Cells were transfected 24 (bar 1 and 2) or 48 h (bar 3 and 4) after the seeding and analyzed 24 (bar 1 and 3) or 48 h (bar 2 and 4) after the transfection. Bright green cells were observed in compact areas of undifferentiated ES colonies on laminin 24 h after transfection (Panels A & B). Transfection at 48 h after initial seeding gave the highest efficiency: 38% of the cells were GFP-positive as determined by FACS analysis 24 h after the transfection (Panel C).

To investigate whether the feeder-free hES cells can undergo stable genetic modification, H1 hES cells maintained on Matrigel® were cotransfected with a mixture of 7.5 μg plasmid carrying β-galactosidase driven by the EF1a promoter, and 2.5 μg of plasmid carrying the PGK promoter driving the neophosphotransferase gene. The cells were transfected 48 h after plating on Matrigel® in mEF-conditioned medium. Ten μg of plasmid plus 15 μL of FuGENE™ (Roche Diagnostics Corp.) was incubated with the cells in 1 mL for 4 h before adding 2.5 mL of mEF-conditioned medium. After 48 h, medium was exchanged for mEF-conditioned medium supplemented with 200 μg/mL geneticin. Cultures were maintained in selection medium with daily medium exchange for over 21 days. All mock-transfected cultures (those receiving FuGENE™ mixed with water rather than plasmid) died within 48-72 h. Drug resistant colonies arose in the wells transfected with both FuGENE™ and plasmid at a frequency of about 1 in $10^5$ originally transfected cells. The colonies were maintained in geneticin-containing mEF-conditioned medium and expanded.

Example 6

Additives that Promote Undifferentiated ES Cell Growth in Fresh Medium

Further experiments were conducted to investigate how different growth factors influence the proliferation and maintenance of undifferentiated hES cells of the H9 cell line.

hES medium contained 20% Serum Replacement (Gibco #10828-028), 80% Knockout DMEM (Gibco #10829-018), 1% non-essential amino acids (Gibco #11140-050), 1 mM L-glutamine (Gibco #15039-027), and 2.5 mM β-mercaptoethanol (Sigma #M7522). This medium was supplemented with 40 ng/mL bFGF; 15 ng/mL stem cell factor (SCF, R&D System #255SC); 100 ng/mL leukemia inhibitory factor (LIF, Sigma #L5283 or Chemicon #LIF 1010); 50 ng/mL ciliary neurotrophic factor (CNTF, R&D system #257-NT); 50 ng/mL recombinant human Oncostatin M (OSM, Sigma #O9635); and 15 ng/mL interleukin 6 (IL-6, R&D System #206-IL).

The H9 cell line (passage 31) was harvested from a culture in conditioned medium, plated onto Matrigel®, and cultured with hES medium with the factors at the concentrations indicated above, or 5- or 25-fold lower. Cells grown in the fully supplemented medium displayed undifferentiated hES morphology. A higher degree of differentiation was observed after 4 passages for the cultures grown at lower concentrations of the growth factors, and the cells maintained without growth factors were almost completely differentiated. These cultures were terminated.

After 6 passages, cells from the full-strength cocktail were replated onto Matrigel® as before, or onto laminin, which is free of the growth factors contained in the Matrigel® matrix. After 8 passages, a large percentage of cells (~50-70%) in cultures grown on Matrigel® or laminin in this medium continued to display undifferentiated hES morphology. Some cells on Matrigel® or laminin were then passaged into hES medium containing added 40 ng/mL bFGF; but not SCF, LIF, CNTF, OSM, or IL-6. The cells continued to show an undifferentiated phenotype for the next 4 passages.

FACS analysis for marker expression was conducted using the following specific antibodies. SSEA 4, clone MC 813 mouse IgG3; Tra-1 60, mouse IgM, Tra-1 81, mouse IgM; SSEA-1, mouse IgM; c-kit, BD PharMingen #555714; R-PE labeled mouse anti-human CD117; mouse IgG1, clone YB5.B8; gp130, R&D System #FAB 228P; R-PE labeled mouse IgG1, clone 28123.111; R-PE labeled isotype control mouse IgG1, PharMingen #33815; isotype control mouse IgG3, Sigma #M3645. Goat anti-mouse IgG3 FITC labeled was obtained from Southern Biotechnology #1102-02.

The cells were washed with warm PBS for 3-5 minutes, incubated with 3 mL 0.5 mM EDTA at 37° C. for 10 min, and collected into a 15-mL tube containing 10 mL medium. They were spun down at 1200 rpm (400 g), washed in 1% BSA/PBS, and suspended in 100 µL of diluted primary antibody at 4° C. for 30 min. After rewashing in 1% BSA/PBS, they were incubated with goat anti-mouse IgG3 FITC (1:100) at 4° C. for 15-30 min, then washed and resuspended in 500 µL 1:1000 propidium iodine.

FIG. 5 (Upper Panel) shows the results of FACS analysis of markers for undifferentiated phenotype for H9 cells maintained for 8 passages in the growth factor mixture. Expression patterns and levels of surface markers, including SSEA-1, SSEA-4, Tra 1-60 and Tra 1-81 in cultures maintained in high concentrations of growth factors were similar to cells maintained in MEF conditioned medium (MEF-CM).

These results confirm that conditioned medium contains factors that promote stem cell growth without differentiation, and that these factors can be either be secreted into the medium by cells being used for the conditioning, or added to the medium artificially.

FIG. 5 (Lower Panel) shows receptor-associated molecules expressed by the H9 cells after 9 passages in MEF-CM (control), or the artificial mixture of growth factors (GF) on either Matrigel® or laminin. The hepatocellular carcinoma cell line HepG2 serves as a positive control for gp130.

All cell lines stained positively for histocompatibility Class I antigen (HLA-ABC), and were negative in the isotype control (msIgG1). 50-70% of cells in cultures maintained in growth factors or MEF-CM expressed c-kit (a receptor for stem cell factor) while less than 20% of cells expressed gp130 (associated with the LIF receptor). In contrast, almost 100% of HepG2 cells expressed gp130. This pattern supports the hypothesis that ligands for c-kit help support undifferentiated hES cell growth.

Cells passaged on Matrigel® in hES medium containing the growth factor cocktail were evaluated for pluripotency. In differentiation medium containing 80% KO-DMEM, 20% FBS, 1 mM glutamine, 0.1 mM β-mercaptoethanol, and 1% non-essential amino acids, the cells readily formed embryoid bodies. After 5 days, the EBs were plated onto gelatin coated plates and differentiated an additional 16 days. They were then fixed in 4% paraformaldehyde, permeabilized with ethanol, blocked with 10% normal goat serum, and then analyzed for phenotypic markers by indirect antibody staining.

Immunocytochemical analysis showed the presence of β-tubulin III in cells having neuronal morphology. Other cells stained for a-fetoprotein or smooth muscle actin. This demonstrates that hES cells cultured in medium comprising SCF and other factors have the capacity to differentiate into derivatives of all three germ layers.

After 14 passages in the full-strength growth factor cocktail (~70 population doublings), about 50-70% of cells cultured on Matrigel® or laminin displayed morphology of undifferentiated hES cells, and had a normal karyotype. Cells cultured without any growth factor showed almost complete differentiation after 4 weeks in culture. A high degree of differentiation was also observed for cultures in which the growth factors had been diluted by 5- or 25-fold.

Additional experiments were done to dissect the components in the factor cocktail essential for hES cell growth. The H9 hES cell line was cultured in non-conditioned ES medium supplemented with bFGF alone at high (40 ng/mL) or low (8 ng/mL) concentration, or bFGF (40 ng/mL) in combination with SCF (15 ng/mL) or Flt-3 ligand (75 ng/mL).

FIG. 6 shows the results. Cultures with high concentrations of bFGF contained ~30-50% cells having undifferentiated morphology, with a higher proportion in cultures also containing SCF or Flt-3 ligand. FACS analysis showed that ~60% of the cells in these cultures expressed SSEA-4. In comparison, cultures in conditioned medium contained ~80% with undifferentiated morphology and ~90% expressing SSEA-4.

In a subsequent experiment, the hES cell line H1 at passage 27 or the H7 line at passage 35 hES cells previously maintained in conditioned medium were cultured in fresh ES medium containing these growth factors.

TABLE 2

| Factors added to fresh ES medium for hES cell culture | | |
|---|---|---|
| Condition | bFGF | Other Growth Factors |
| A | 8 ng/mL | |
| B | | |
| C | 40 ng/mL | |
| D | 40 ng/mL | SCF (15 ng/mL) |
| E | 40 ng/mL | Flt-3L (75 ng/mL) |
| F | 40 ng/mL | TPO (100 ng/mL) |
| G | 40 ng/mL | LIF (100 ng/mL) |
| H | 40 ng/mL | SCF (15 ng/mL), IL-6 (15 ng/mL), LIF (100 ng/mL), CNTF (50 ng/mL), OSM (50 ng/mL) |
| I | | SCF (15 ng/mL) |
| J | | SCF (100 ng/mL) |
| K | | Flt-3L (75 ng/mL) |
| L | | TPO (100 ng/mL) |
| M | | SCF (15 ng/mL), Flt-3L (75 ng/mL) |
| N | | SCF (15 ng/mL), TPO (100 ng/mL) |
| O | | SCF (100 ng/mL), Flt-3L (100 ng/mL), IL-6 (15 ng/mL) |

TABLE 2-continued

Factors added to fresh ES medium for hES cell culture

| Condition | bFGF | Other Growth Factors |
|---|---|---|
| P | 40 ng/mL | SCF (15 ng/mL), Flt-3L (75 ng/mL) |
| Q | 40 ng/mL | SCF (15 ng/mL), TPO (100 ng/mL) |

Cultures were passaged in these conditions and evaluated on an ongoing basis by morphological criteria. Many of the conditions continued to maintain considerable numbers of undifferentiated colonies. FIG. 7 shows expression of SSEA-4 as evaluated by flow cytometry (gated for low or high staining level) at passage 9 (H7 cells) or passage 10 (H1 cells) after being transferred from conditioned medium. H7 cells grown in any of these conditions showed telomerase activity at passage 15.

Example 7

Other Base Media for Growing hES Cells in Feeder-Free Culture hES cells passaged 29 times in conditioned medium were weaned onto an alternative medium designed for proliferation and development of hematopoietic cells.

Ex vivo expansion medium was obtained by arrangement with a commercial supplier, and is thought to be based on the medium described in U.S. Pat. No. 5,405,772 (Ponting, Amgen Inc.). The Ponting medium comprises the following components: Iscove's modified Dulbecco's medium; amino acids; vitamins; bovine albumin; bovine transferrin (100 µg/mL); lipids and cholesterol; β-mercaptoethanol; pyruvate; nucleotides; epidermal growth factor (15 ng/mL); fibroblast growth factor (2 ng/mL); platelet-derived growth factor (10 ng/mL), and insulin (10 µg/mL). For use in the current experiments, the medium was further supplemented with 2 mM L-glutamine, 1% non-essential amino acids (Gibco), 0.1 mM β-mercaptoethanol, and 8 ng/mL bFGF.

The cells were first passaged onto Matrigel® coated plates using collagenase IV, and cultured for 2 days with conditioned medium. On day 2, the 100% conditioned medium was replaced with medium containing 80% conditioned medium plus 20% fresh expansion medium. Cells were fed fresh daily and passaged weekly. The proportion of expansion medium was increased by 20% approximately every 2 days until the cells were completely weaned, and then grown until they had been passaged a further 8 times.

At passages 1-4 in the expansion medium, the proportion of cells with the morphology of undifferentiated phenotype appeared to diminish slightly, but was restored by passage 8. When these cells were passaged back to medium conditioned by primary mouse embryonic fibroblasts, the cells were indistinguishable from those grown throughout the period in conditioned medium by the second passage.

To confirm that these cells retained their pluripotency, embryoid bodies were formed and analyzed by immunocytochemistry for phenotypic markers representing each of the three germ layers. After passage 4 in expansion medium, the cells were dissociated into small clumps using 200 U/mL collagenase IV at 37° C. for 10 min placed in suspension culture in differentiation medium (DMEM+10% FBS) for 4 days, then transferred onto poly-L-ornithine hydrobromide coated plates and cultured a further 10 days. They were fixed in 4% paraformaldehyde, permeabilized, and labeled alternately with mouse anti human β-tubulin isotype III clone SDL.3D10, mouse anti human muscle actin clone HHF35, or mouse anti a-fetoprotein. Primary antibody was visualized using FITC labeled goat anti-mouse IgG. Results showed that hES cells passaged repeatedly in expansion medium (not previously conditioned), and then differentiated, were positive for β-tubulin and muscle actin.

Example 8

Rapid Expansion Method for Producing Pluripotent Stem Cells hES cells passaged 20 times in conditioned medium were weaned onto an alternative medium designed for proliferation of human hematopoietic cells. X-VIVO™ 10 expansion medium was obtained from Biowhittaker; QBSF™-60 was obtained from Quality Biological Inc. The X-VIVO™ 10 formulation contains pharmaceutical grade human albumin, recombinant human insulin and pasteurized human transferrin. Exogenous growth factors, artificial stimulators of cellular proliferation or undefined supplements are not included in the X-VIVO™ 10 medium. They are also devoid of any protein-kinase C stimulators. QBSF™-60 is a serum-free formulation that contains recombinant or pasteurized human proteins. For use in these experiments, the X-VIVO™ 10 medium was supplemented with 2 mM L-glutamine, 1% non-essential amino acids (Gibco), 0.1 mM β-mercaptoethanol, and 8 ng/mL bFGF. The medium was further supplemented with 8 ng/mL or 40 ng/mL of bFGF (Gibco); 40 ng/mL of bFGF and 15 ng/mL of SCF (R & D System); or 40 ng/mL of bFGF and 75 ng/mL of Flt3 ligand (R & D System). QBSF™-60 medium was supplemented with 0.1 mM β-mercaptoethanol, 1% non-essential amino acids (Gibco) and 40 ng/mL of bFGF. hES cells cultured in mEF conditioned medium was used as control in these experiments.

The hES cells were first passaged onto Matrigel® coated plates using collagenase IV, and cultured for 2 days with conditioned medium. On day 2, the conditioned medium was replaced with 80% unconditioned ES medium plus 20% expansion medium. Cells were fed fresh daily and passaged weekly. The proportion of expansion medium was increased by 20% approximately every 2 days until the cells were completely weaned, and then grown until they had been passaged 6 more times.

FIG. 8 shows colonies of hES cell at the end of 6 passages (sufficient for full adaptation) in the following media: (A) mEF conditioned medium+bFGF (8 ng/mL); (B) X-VIVO™ 10+bFGF (40 ng/mL); (C) X-VIVO™ 10+bFGF (40 ng/mL)+stem cell factor (SCF, Steel factor) (15 ng/mL); (D) X-VIVO™ 10+bFGF (40 ng/mL)+Flt3 ligand (75 ng/mL); (E) QBSF™-60+bFGF (40 ng/mL).

The following table shows the average total cell expansion per passage, for undifferentiated hES cells cultured for 4 passages in mEF conditioned medium, or for 7 passages in X-VIVO™ 10 or QBSF™-60.

TABLE 3

Growth Rates for ES Cell Cultures

| Medium | Average Cell Expansion per Passage |
|---|---|
| mEF conditioned medium | 2.2 fold |
| X-VIVO ™ 10 + bFGF (40 ng/mL) | 6.0 fold |
| X-VIVO ™ 10 + bFGF (40 ng/mL) + SCF (15 ng/mL) | 8.2 fold |

TABLE 3-continued

Growth Rates for ES Cell Cultures

| Medium | Average Cell Expansion per Passage |
|---|---|
| X-VIVO ™ 10 + bFGF (40 ng/mL) + Flt3 ligand (75 ng/mL) | 5.0 fold |
| QBSF ™-60 + bFGF (40 ng/mL) | 6.4 fold |

The average expansion of cells per passage in X-VIVO™ 10 and QBSF™-60 was greater than the cells cultured in mEF conditioned medium culture. The cells in mEF conditioned medium were passaged on average every 7 days, while the cells in X-VIVO™ 10 and QBSF™-60 were passaged on average every 5 days. Thus, the rate of expansion in unconditioned X-VIVO™ 10 or QBSF™-60 was ~3.2 to 5.2 times faster than in mEF conditioned ES medium.

FIG. 9 shows the gene expression profile of hTERT and Oct3/4. The RNA was isolated from the cells using High Pure RNA Isolation Kit (Roche Diagnostics) and evaluated by Taqman™ assay (real time RT-PCR). The gene expression in each of the test condition is plotted relative to expression in the control culture. Taking into consideration the instrument error and assay variability, differences in expression between the test and control samples are only significant if greater than 2-fold. The analysis shows expression of hTERT and Oct-3/4 decreases somewhat upon adaptation to unconditioned X-VIVO™ 10 or QBSF™-60 medium (first four bars in each set), but returns to standard levels when the cells are passaged back into mEF conditioned medium (last three bars in each set).

To confirm that cells cultured in unconditioned medium retain their pluripotency, embryoid bodies were formed and analyzed by immunocytochemistry for phenotypic markers representing each of the three germ layers. After passage 7 in expansion medium, the cells were dissociated into small clumps using 200 U/mL collagenase IV at 37° C. for 10 min, placed in suspension culture in differentiation medium (DMEM+10% FBS) for 4 days, then transferred onto poly-L-ornithine hydrobromide coated plates for a further 10 days. They were fixed in 4% paraformaldehyde, permeabilized, and labeled by immunocytochemistry.

FIG. 10 shows the results. hES cells passaged 7 times in unconditioned X-VIVO™ 10 medium stained for α-fetoprotein (representing endoderm); muscle actin (representing mesoderm), and β-tubulin III (representing ectoderm).

These results show that hES cells can be expanded in fresh (non-conditioned) media in a feeder-free environment at a rapid rate suitable for commercial production. The cells retain the morphology of undifferentiated hES cells, and can be differentiated into derivative cells representing all three germ layers.

The compositions and procedures provided in the description can be effectively modified by those skilled in the art without departing from the spirit of the invention embodied in the claims that follow.

What is claimed as the invention is:

1. A method of expanding primate pluripotent stem cells (pPS cell) in an undifferentiated state comprising a) attaching a pPS cell to a microcarrier comprising a matrix and b) providing the pPS cells with a nutrient media and c) expanding 2 fold the pPS cells in an undifferentiated state.

2. The method of claim 1, wherein the matrix comprises an extracellular matrix protein.

3. The method of claim 1, wherein the matrix comprises a soluble preparation of Engelbreth-Holm-Swarm tumor.

4. The method of claim 1, wherein the nutrient media comprises 20% fetal bovine serum.

5. The method of claim 1, wherein the nutrient media comprises 20% serum replacement.

6. The method of claim 1, wherein the nutrient media comprises albumin.

7. The method of claim 1, wherein the nutrient media comprises insulin,

8. The method of claim 1, wherein the nutrient media comprises transferrin.

9. The method of claim 1, wherein the nutrient media is a media conditioned by a cell.

10. The method of claim 1, wherein the nutrient media is non-conditioned media comprising fibroblast growth factor (FGF).

11. The method of claim 10 wherein the FGF is FGF 2.

12. The method of claim 10, wherein the FGF is FGF 4.

13. A method of expanding cells expressing the markers Oct 4, stage specific antigen 4 (SSEA4), Tra-1-60 and Tra-1-81 in an undifferentiated state comprising a) attaching cells expressing the markers Oct 4, stage specific antigen 4 (SSEA4), Tra-1-60 and Tra-1-81 to a microcarrier comprising a matrix and b) providing the cells expressing the markers Oct 4, stage specific antigen 4 (SSEA4), Tra-1-60 and Tra-1-81 with a nutrient media and c) expanding 2 fold the cells expressing, the markers Oct 4, stage specific antigen 4 (SSEA4), Tra-1-60 and Tra-1-81 in an undifferentiated state.

14. The method of claim 13, wherein the matrix comprises an extracellular matrix protein.

15. The method of claim 13, wherein the matrix comprises a soluble preparation of Engelbreth-Holm-Swarm tumor.

16. The method of claim 13, wherein the nutrient media comprises 20% fetal bovine serum.

17. The method of claim 13, wherein the nutrient media comprises 20% serum replacement.

18. The method of claim 13, wherein the nutrient media comprises albumin.

19. The method of claim 13, wherein the nutrient media comprises insulin.

20. The method of claim 13, wherein the nutrient media comprises transferrin.

21. The method of claim 13, wherein the nutrient media is a media conditioned by a cell.

22. The method of claim 13, wherein the nutrient media is non-conditioned media comprising fibroblast growth factor (FGF).

23. The method of claim 13 wherein the FGF is FGF 2.

24. The method of claim 13, wherein the FGF is FGF 4.

* * * * *